US012636408B2

(12) United States Patent
Danilkovitch

(10) Patent No.: US 12,636,408 B2
(45) Date of Patent: *May 26, 2026

(54) ADIPOSE COMPOSITIONS AND METHODS OF USE THEREOF

(71) Applicant: BRITECYTE INC., Columbia, MD (US)

(72) Inventor: Alla Danilkovitch, Columbia, MD (US)

(73) Assignee: BRITECYTE INC., Frederick, MD (US)

( * ) Notice: Subject to any disclaimer, the term of this patent is extended or adjusted under 35 U.S.C. 154(b) by 408 days.

This patent is subject to a terminal disclaimer.

(21) Appl. No.: 17/887,013

(22) Filed: Aug. 12, 2022

(65) Prior Publication Data

US 2023/0063467 A1     Mar. 2, 2023

Related U.S. Application Data

(60) Provisional application No. 63/232,465, filed on Aug. 12, 2021.

(51) Int. Cl.
A61L 27/36          (2006.01)

(52) U.S. Cl.
CPC ............................... A61L 27/3691 (2013.01)

(58) Field of Classification Search
CPC ................................................ A61L 27/3691
USPC ......................................................... 424/574
See application file for complete search history.

(56) References Cited

U.S. PATENT DOCUMENTS

| | | | |
|---|---|---|---|
| 7,890,183 B2 | 2/2011 | Palti | |
| 10,596,201 B2 | 3/2020 | Huang | |
| 2008/0195230 A1 | 8/2008 | Quijano | |
| 2010/0279405 A1* | 11/2010 | Peterson | C12N 5/0653 |
| | | | 435/297.1 |
| 2011/0008300 A1* | 1/2011 | Wouters | A61P 3/10 |
| | | | 435/325 |
| 2011/0151011 A1 | 6/2011 | Flynn | |
| 2012/0264190 A1 | 10/2012 | Christman | |
| 2014/0234272 A1 | 8/2014 | Vesey | |
| 2015/0044179 A1 | 2/2015 | Saeki | |
| 2016/0101200 A1* | 4/2016 | Chitre | A61L 2/08 |
| | | | 424/574 |
| 2017/0021058 A1 | 1/2017 | Huang et al. | |
| 2018/0117088 A1 | 5/2018 | Cao et al. | |
| 2018/0127719 A1 | 5/2018 | Nahas et al. | |
| 2019/0076582 A1 | 3/2019 | Connor | |
| 2019/0111183 A1 | 4/2019 | Xu | |
| 2019/0298885 A1 | 10/2019 | Schilling | |
| 2022/0032934 A1 | 2/2022 | Zhang | |
| 2022/0073881 A1 | 3/2022 | Nahas | |
| 2022/0339196 A1 | 10/2022 | Rho et al. | |
| 2023/0044236 A1 | 2/2023 | Kim | |
| 2023/0063467 A1 | 3/2023 | Danilkovitch | |
| 2024/0261471 A1 | 8/2024 | Danilkovitch | |

FOREIGN PATENT DOCUMENTS

| | | |
|---|---|---|
| WO | WO 2021/045595 A1 | 3/2021 |
| WO | WO 2023/287892 A1 | 1/2023 |

OTHER PUBLICATIONS

Cheung et al., Composite hydrogel scaffolds incorporating decellularized adipose tissue for soft tissue engineering with adipose-derived stem cells, Biomaterials, vol. 35, (2014), pp. 1914-1923.*
Bush-Joseph et al., Effect of Tibial Attachment Location on the Healing of the Anterior Cruciate Ligament Freeze Model, Journal of Orthopaedic Research, vol. 14, (1996), pp. 534-541.*
Flynn, The use of decellularized adipose tissue to provide an inductive microenvironment for the adipogenic differentiation of human adipose-derived stem cells, Biomaterials, vol. 31, (2010), pp. 4715-4724.*
U.S. Appl. No. 63/232,465, filed Aug. 12, 2021, Danilkovitch.
U.S. Appl. No. 63/221,248, filed Jul. 17, 2022, Danilkovitch.
PCT/US22/36982, Oct. 4, 2022, Danilkovitch.
International Search Report and Written Opinion mailed on Oct. 5, 2022 by International Searching Authority for Patent Application No. PCT/US22/36982, which was filed on Jul. 13, 2022 (Inventor—Danilkovitch et al.; Applicant—Britecyte Inc.) (8 pages).
Rossi. "Decoration of RGD-mimetic porous scaffold with engineered, devitalized adipose matrix." Acta Biomaterialia. Dec. 18, 2016, p. 192.
Chun, S.Y., et al., "Optimization of extracellular matrix extraction from human perirenal adipose tissue," Journal of Biomaterials, 35(9): 1180-1191 (2021).
Chun, S.Y., "Optimal delipidation solvent to secure extracellular matrix from human perirenal adipose tissue," Journal of Biomedical Materials Research, (2021), Abstract.
Flynn, L.E., "The use of decellularized adipose tissue to provide an inductive microenvironment for the adipogenic differentiation of human adipose-derived stem cells," Biomaterials, 31(17): 4715-4724 (2010).
Guo, L., et al., "Comparison of adipose tissue cellularity in chicken lines divergently selected for Fatness," Poultry Science, 90(9): 2024-2034 (2010).

(Continued)

*Primary Examiner* — Jennifer M. H. Tichy
(74) *Attorney, Agent, or Firm* — BALLARD SPAHR LLP

(57) ABSTRACT

Disclosed are devitalized adipose tissue. Disclosed are compositions comprising devitalized adipose tissue. In some aspects, the compositions further comprise a cryopreservation or lyophilization solution. Disclosed are cryopreserved or lyophilized devitalized adipose tissue. Disclosed are methods of augmenting a soft tissue site of a subject in need thereof comprising administering to the subject a composition comprising devitalized adipose tissue. Disclosed are methods of treating a subject having fat pad atrophy comprising administering to the subject a composition comprising devitalized adipose tissue. Disclosed are methods of treating a subject having lipodystrophy comprising administering to the subject a composition comprising devitalized adipose tissue. Disclosed are methods of treating a subject having a metabolic disease or condition comprising administering to the subject a composition comprising devitalized adipose tissue.

14 Claims, 32 Drawing Sheets

(56) References Cited

OTHER PUBLICATIONS

Moon, J., et al., "Brown adipose tissue ameliorates autoimmune arthritis via inhibition of Th17 cells," Scientific Reports, 10:12374 (2020).

Niazli, N., "Autologous Micro Fragmented Adipose Cell Therapy for End-Stage Ankle Osteoarthritis—Case Report and Review of Literature," SN Comprehensive Clinical Medicine, 3: 909-913 (2021).

Vargel, I., et al., "Autologous Adipose-Derived Tissue Stromal Vascular Fraction (AD-tSVF) for Knee Osteoarthritis," Int. J. Mol. Sci., 23: 13517 (2022), 32 Pages.

Wang, L., et al., "Combining decellularized human adipose tissue extracellular matrix and adipose-derived stem cells for adipose tissue engineering," Acta Biomaterialia, 9(11):8921-8931 (2013).

Wang, J.K., et al., "Supercritical carbon dioxide extracted extracellular matrix material from adipose tissue," Materials Science and Engineering, C75: 349-358 (2017).

Wu, I., et al., "An Injectable Adipose Matrix for Soft Tissue Reconstruction," 129(6): 1247-1257 (2012).

Kim, D.Y., et al., "Cryopreservation of lipoaspirates: in vitro measurement of the viabiity of adipose-derived stem cell and lipid peroxidation," Int. Wound J., pp. 1-9 (2020).

Menzi, N., et al., Wet milling of large quantities of human excision adipose tissue for the isolation of stromal vascular fraction cells, Cytotechnology, 70: 807-817 (2018).

Osinga, R., et al., "Effects of Intersyringe Processing on Adipose Tissue and Its Cellular Components: Implications in Autologous Fat Grafting," Plastic and Reconstructive Surgery, 135(6): 1618 (2015).

Rao, P., et al., "Structural and Functional Characterization of Deceased Donor Stem Cells: A Viable Alternative to Living Donor Stem Cells," Hindawi, Stem Cells International, 13 Pages (2019).

Schafer, M.E., et al., "Acute Adipocyte Viability After Third-Generation Ultrasound-Assisted Liposuction," Aesthetic Surgery Journal, 33(5): 698-704 (2013).

Urbonas, T., et al., "Assessing Adipocyte Viability and Surgeons' Work Efficiency by Comparing Different Liposuction Methods," Plastic Reconstr. Surg. Glob. Open, 9 Pages (2023).

* cited by examiner

Living Donor, cryopreserved 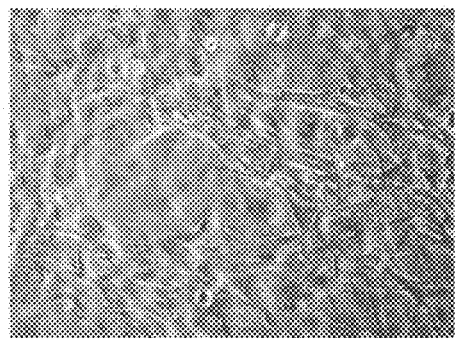   Cadaveric Donor, cryopreserved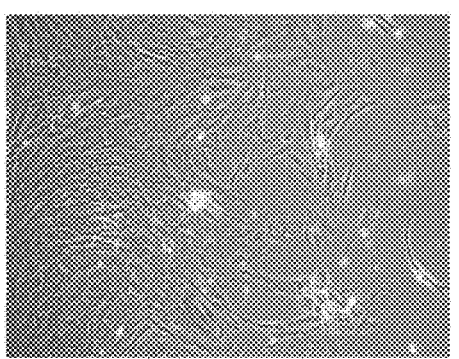
FIG. 3

A

| | Living donor#1 | Control | +LPS |
|---|---|---|---|
| 1 | Devitalized processed adipose | 3.64 | 3.74 |
| 2 | Fresh processed adipose | 4.45 | 37.01 |
| 3 | Adipocytes from fresh adipose | 1.94 | 5.053 |
| 4 | SVF cells from fresh adipose | 12.004 | 57.307 |
| 5 | Cryopreserved processed adipose | 3.28 | 9.85 |
| 6 | Adipocytes from cryopreserved adipose | 0.429 | 0.869 |
| 7 | SVF cells from cryopreserved adipose | 1.457 | 14.185 |
| | Cadaveric donor #3 | | |
| 1 | Devitalized processed adipose | 3.13 | 3.18 |
| 2 | Fresh processed adipose | 3.16 | 543.18 |
| 3 | Adipocytes from fresh adipose | 1.050 | 5.728 |
| 4 | SVF cells from fresh adipose | 3.807 | 79.847 |
| 5 | Cryopreserved processed adipose | 3.33 | 3.06 |
| 6 | Adipocytes from cryopreserved adipose | 0.566 | 0.685 |
| 7 | SVF cells from cryopreserved adipose | 2.426 | 23.706 |

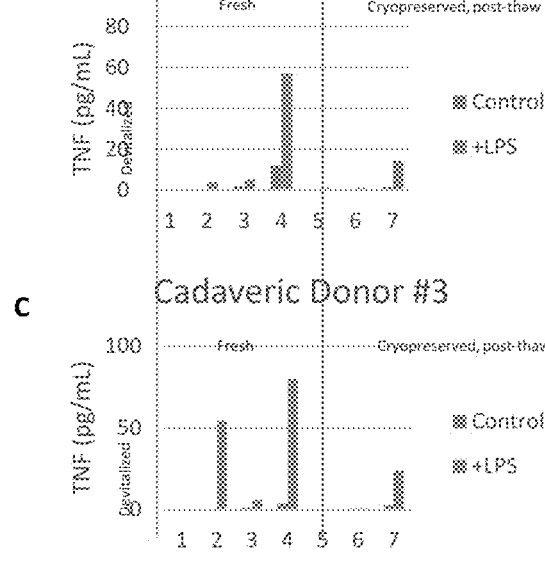

FIG. 4A, FIG. 4B, FIG. 4C

Cryopreserved,
post-thaw

Lyophilized, post-
rehydration

In vials

In PBS drop

Fresh adipose starting material
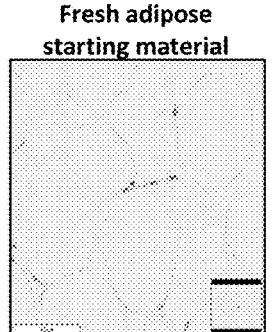
Processed adipose prior to preservation
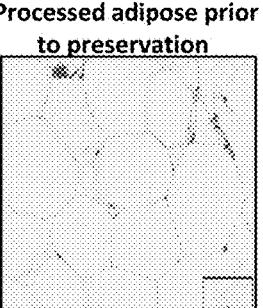
Lyophilized adipose after rehydration
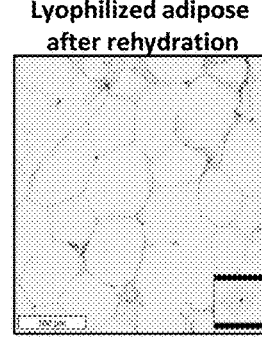
Cryopreserved adipose post-thaw
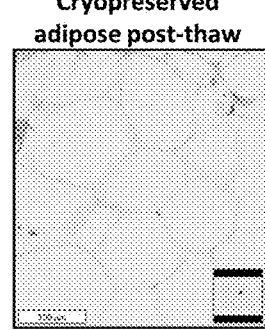
FIG. 7

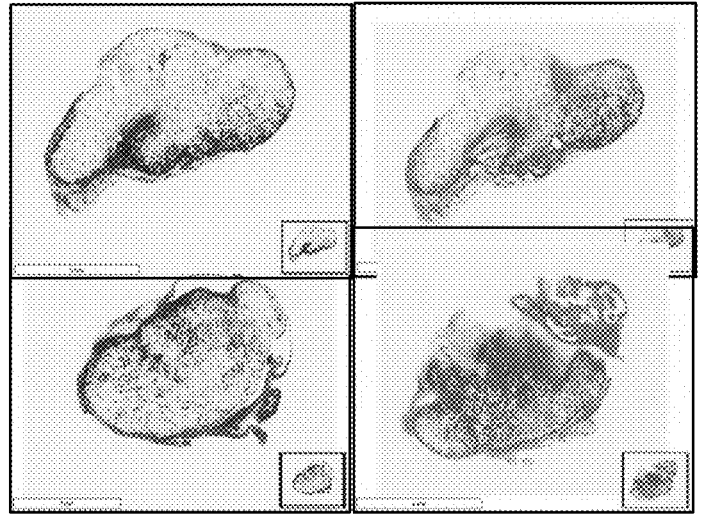
Low magnification
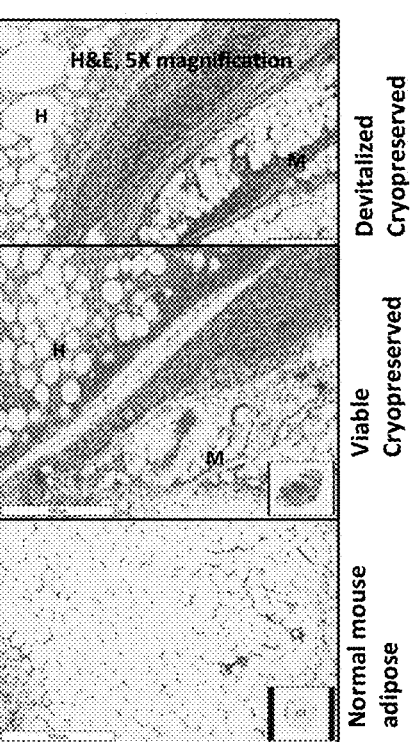
FIG. 11

Human NALM-6 cell line positive control

Cells # (thousand):    25    12.5    6.3    3.1    1.6    0.8    0.4    0.2    0.1

Lyophilized

Cryopreserved

Protein standard molecular weight (kDa)

220

120
100

80

60

50

40

30

20

4-12% gradient gel/WB Human KU-80 Marker

Graft A
Graft B
Graft C
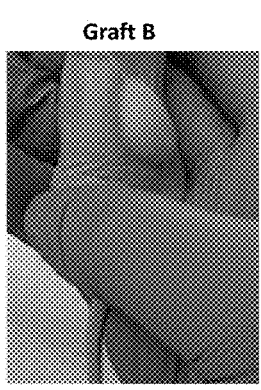
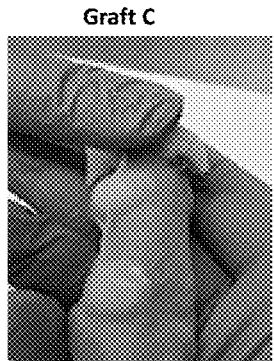
FIG. 19

Graft A          Graft B          Graft C
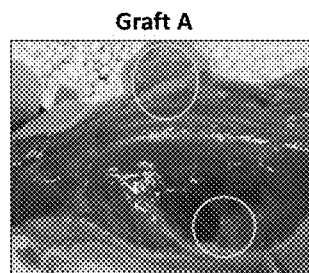 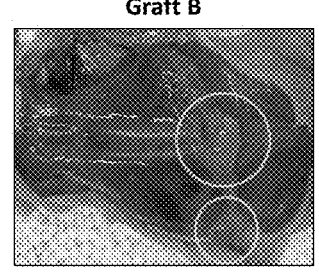 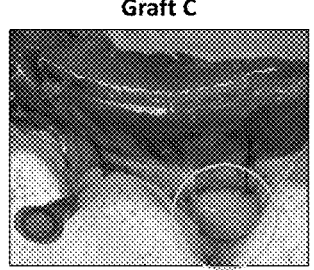
FIG. 21
Graft A          Graft B          Graft C
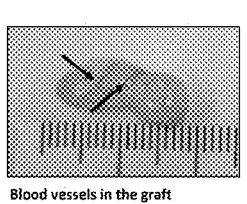
Blood vessels in the graft
from mouse #8
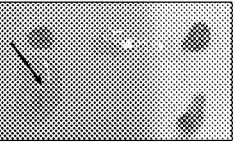
Oil released in the cut
graft from mouse #3
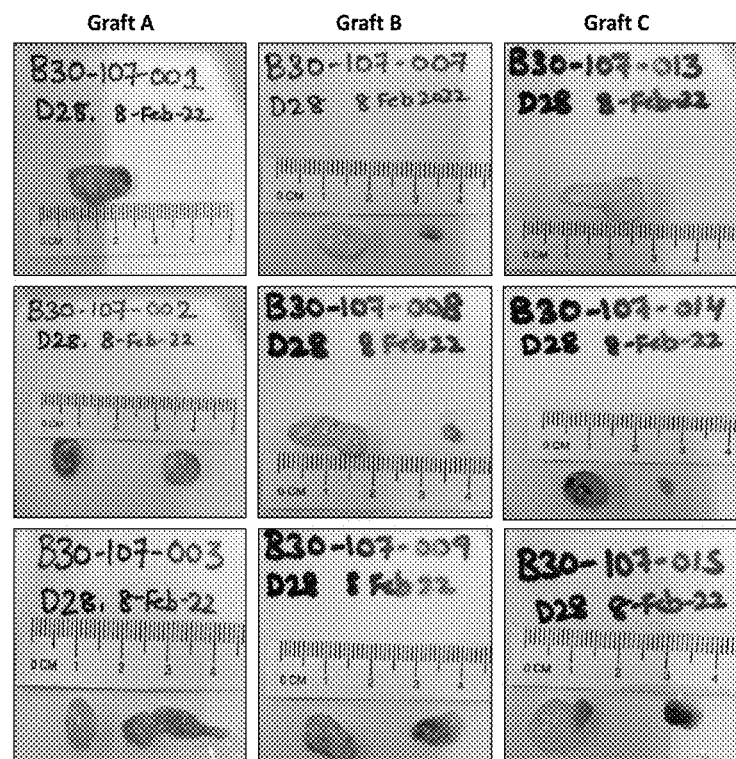
FIG. 22

Oil released from the cut
graft in mouse #10

Blood vessels in the graft
from mouse #17

A pus-like substance released
from the cut graft in mouse
18. There was no smell or
bacteria upon microscopic
exam indicating aseptic
inflammation.

| Graft # | 4 Weeks | | | 8 Weeks | | |
|---|---|---|---|---|---|---|
| | Adipose Graft Type: | | | Adipose Graft Type: | | |
| | A | B | C | A | B | C |
| 1 | 0.1470# | 0.0143 | 0.4614# | 0.0396 | 0.0594 | 0.2151 |
| 2 | Fused with graft 1 | 0.2280 | Fused with graft 1 | 0.3335 | 0.4256 | 0.0863 |
| 3 | 0.2198 | 0.0105 | 0.2814 | 0.1460 | 0.0396 | 0.0797 |
| 4 | 0.2170 | 0.2254 | 0.0080 | 0.1389 | 0.3130 | 0.5200** |
| 5 | 0.1410 | 0.0835 | 0.3670 | 0.2296 | 0.1657 | 0.0277 |
| 6 | 0.1600 | 0.2107 | 0.0440 | 0.1725 | 0.0878 | 0.8986** |
| Mean | 0.1470 | 0.1290 | 0.1940 | 0.1770 | 0.1820 | 0.3050 |
| SD | 0.0800 | 0.1050 | 0.2020 | 0.0990 | 0.1560 | 0.3410 |
| Median | 0.1600 | 0.1470 | 0.2810 | 0.1590 | 0.1270 | 0.0860 |
| Graft resorption (in % from the baseline)* | 67% | 71% | 57% | 61% | 60% | 32% |

FIG. 25

| Histological Evaluation | | Histological Scores*<br>(Mean ± SD for 4 & 8 Weeks Combined) | | |
|---|---|---|---|---|
| Tissue Characteristics | Assessment Criteria of Tissue Sections | Graft A | Graft 8 | Graft C |
| Adipose | Fat small droplets | 1.3 ± 0.82 | 0.83 ± 0.72 | 0.58 ± 0.90 |
| Degrading Adipocytes | Fat large droplets | 2.10 ± 1.10 | 2.00 ± 0.43 | 2.08 ± 1.16 |
| Cysts | Large clear spaces | 2.60 ± 1.07 | 3.25 ± 0.97 | 3.17 ± 0.94 |
| | Number of large sized cysts | 0 | 4 | 5 |
| Encapsulated Cysts | Presence of capsule | 0 | 0 | 2 |
| Fibrous Connective Tissue | Collagen fibers | 2.40 ± 0.70 | 2.83 ± 0.94 | 2.83 ± 0.83 |
| Inflammation | Tissue infiltration by histiocytes, neutrophils, lymphocytes | 2.00 ± 0.00 | 1.83 ± 0.58 | 2.42 ± 0.90 |
| M2 macrophages | CD206 ICH positive cells | 2.40 ± 0.52 | 2.75 ± 0.45 | 3.00 ± 0.85 |
| New Blood vessels | CD31 ICH positive cells | 2.00 ± 0.00 | 1.58 ± 0.67 | 1.42 ± 1.08 |

FIG. 28

Fibrous connective tissue formation
Sterile abscess, encapsulated
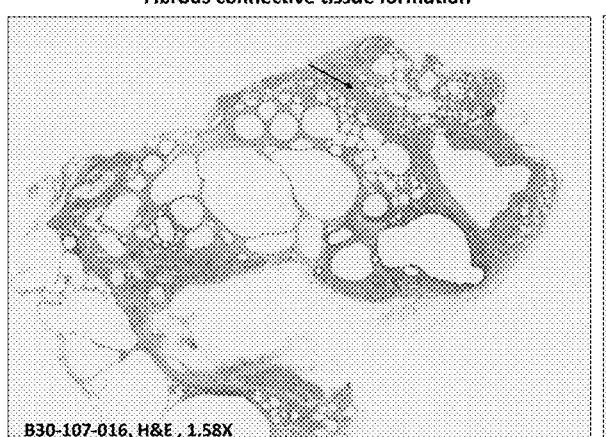
B30-107-016, H&E , 1.58X
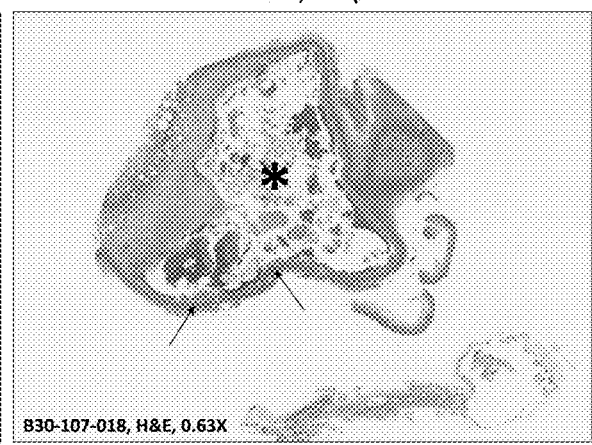
B30-107-018, H&E, 0.63X
FIG. 30

Angiogenesis          Focal Angiogenesis          M2 macrophages

B30-107-016, H&E , 26X     B30-107-016, CD31 ICH, 20X     B30-107-014, CD206 ICH, 20X

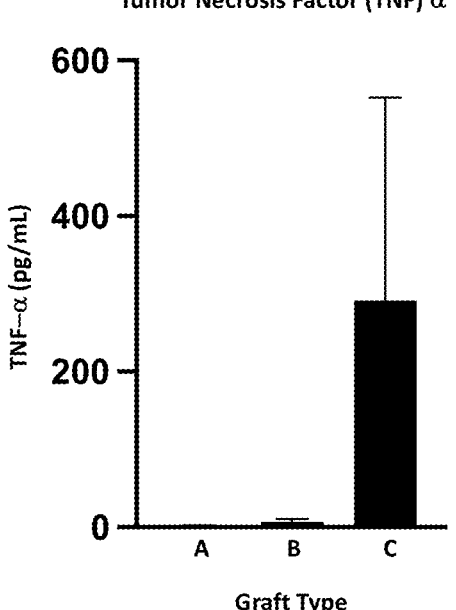
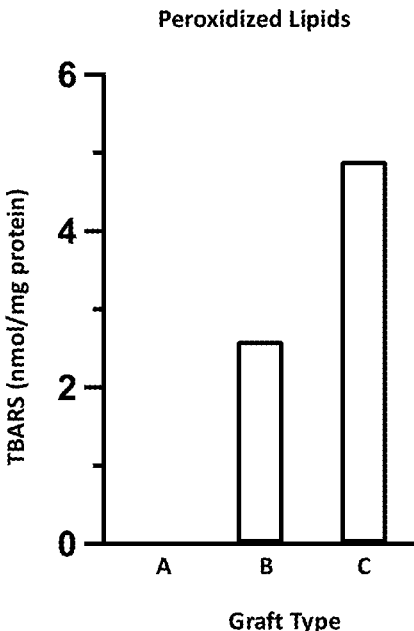
FIG. 32

ADIPOSE COMPOSITIONS AND METHODS OF USE THEREOF

CROSS-REFERENCE TO RELATED APPLICATIONS

This application claims the benefit of U.S. Provisional Patent Application No. 63/232,465, filed on Aug. 12, 2021, which is incorporated by reference herein in its entirety.

BACKGROUND

Reconstruction of soft tissue defects that restore aesthetic appearance and tissue functionality is important for patients with cancer, trauma, lipodystrophy/atrophy or congenital defects. However, current options are limited and all have drawbacks.

Adipose (fat) grafting has been used for reconstructive procedures for more than 100 years. Adipose is an ideal material for soft tissue reconstruction; however, the uses are limited to only autologous adipose, which requires a surgical procedure to harvest patient's adipose tissue followed by a grafting of the collected adipose in an area of soft tissue defects. Moreover, the treatment outcome is highly variable, often requiring re-treatment.

Adipose tissue is vascularized with a large number of immune, endothelial and other types of cells making adipose tissue highly immunogenic. Studies in rodents demonstrated that transplantation of allogeneic fresh adipose between different mouse or rat strains leads to the adipose graft rejection. Therefore, current conventional wisdom is that it is not possible to use allogeneic adipose.

Another conventional wisdom is that high cell viability is critical for adipose graft survival and the outcome of the treatment. However, many studies demonstrate that in free adipose grafts adipocytes die on Day 1 and will be replaced overtime by newly formed adipocytes and by fibrous connective tissue.

BRIEF SUMMARY

Disclosed herein are allogeneic lyophilized and cryopreserved adipose tissue compositions that have low immunogenicity and can be broadly applied for soft tissue defects without requirements for immunosuppression or matching between a donor and a patient. The disclosed compositions can be utilized for soft tissue reconstructive and cosmetic procedures including but not limited to congenital defects, tumor removal sites, burns and scars, chronic wounds, facial and hand rejuvenation, fat pad atrophy, congenital and acquired lipodystrophy, and traumatic injuries.

Disclosed are devitalized adipose tissue. Disclosed are compositions comprising devitalized adipose tissue. In some aspects, the compositions further comprise a cryopreservation or lyophilization solution.

Disclosed are cryopreserved or lyophilized devitalized adipose tissue.

Disclosed are methods of augmenting a soft tissue site of a subject in need thereof comprising administering to the subject a composition comprising devitalized adipose tissue.

Disclosed are methods of treating a subject having fat pad atrophy comprising administering to the subject a composition comprising devitalized adipose tissue.

Disclosed are methods of treating a subject having lipodystrophy comprising administering to the subject a composition comprising devitalized adipose tissue.

Disclosed are methods of treating a subject having a metabolic disease or condition comprising administering to the subject a composition comprising devitalized adipose tissue.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 3 shows presence of viable cells in the cryopreserved tissue confirmed by ex vivo growth of the isolated cells from the processed tissue stromal vascular fraction (SVF) cells.

FIGS. 4A-4C show results of in vitro LPS challenge immunogenicity assay development for living donor #1 and for cadaveric donor #3: table with sample description and numerical values (FIG. 4A), results for living donor (FIG. 4B) and results for cadaveric donors (FIG. 4C).

FIG. 7 shows images of Hematoxylin-Eosin (H&E)-stained human adipose tissue samples at 20× magnification.

FIG. 11 shows Masson's Trichrome (MT) and Hematoxylin & Eosin (H&E) histological staining of dissected cryopreserved devitalized and viable human adipose tissue grafts 4 weeks post-implantation. M—newly formed normal mouse adipose; H—necrotic human adipose graft.

FIG. 19 shows an example of each mouse that received 2×~0.5 cc adipose grafts subcutaneously in the upper and lower parts of the back via a bolus injection. Pictures show animals immediately after injection of adipose grafts.

FIG. 21 shows an example of visual appearance of adipose grafts A (mouse B30-107-004), B (mouse B30-107-011), and C (mouse B30-107-018) at week 8 post-injection (in yellow circles).

FIG. 22 shows visual appearance of excised adipose grafts A, B, and C at week 4 post-injection (on the right). On the left: the upper image—an example of blood vessels in one of the grafts B excised from mouse B30-107-008; the lower image—an example of oil released in graft A from mouse B30-107-003. Two grafts were "fused" together in mouse B30-107-001 (Graft A) and in mouse B30-107-013 (Graft C).

FIG. 25 shows a table of adipose graft weights at weeks 4 and 8 post-injection.

FIG. 28 shows a table of histological scores statistics. *Scoring: 0, none; 1, minimal; 2, mild; 3, moderate; 4, severe. Both scoring and evaluation criteria were defined by an independent pathologist.

FIG. 30 shows images selected by the study pathologist to demonstrate formation of fibrous connective tissue in grafts and the presence of a sterile abscess in graft C from mouse B30-107-018. On the left image: an arrow points to the pink colored collagen rich area of the graft. On the right image: arrows point to the fibrous cyst capsule, and the asterisk shows the cavity of the cyst.

FIG. 32 shows that implantation of radiated adipose grafts (B and C) induces inflammation, which is dose-dependent. The bar graph on the left shows mean+/−SD of inflammatory cytokine TNF-α detected in grafts. The bar graph on the right shows levels of peroxidized lipids detected by the presence of Thiobarbituric Acid Reactive Substances (TBARS) in adipose graft's lysates.

DETAILED DESCRIPTION

Figures 1A, 1B, 1C, 1D:
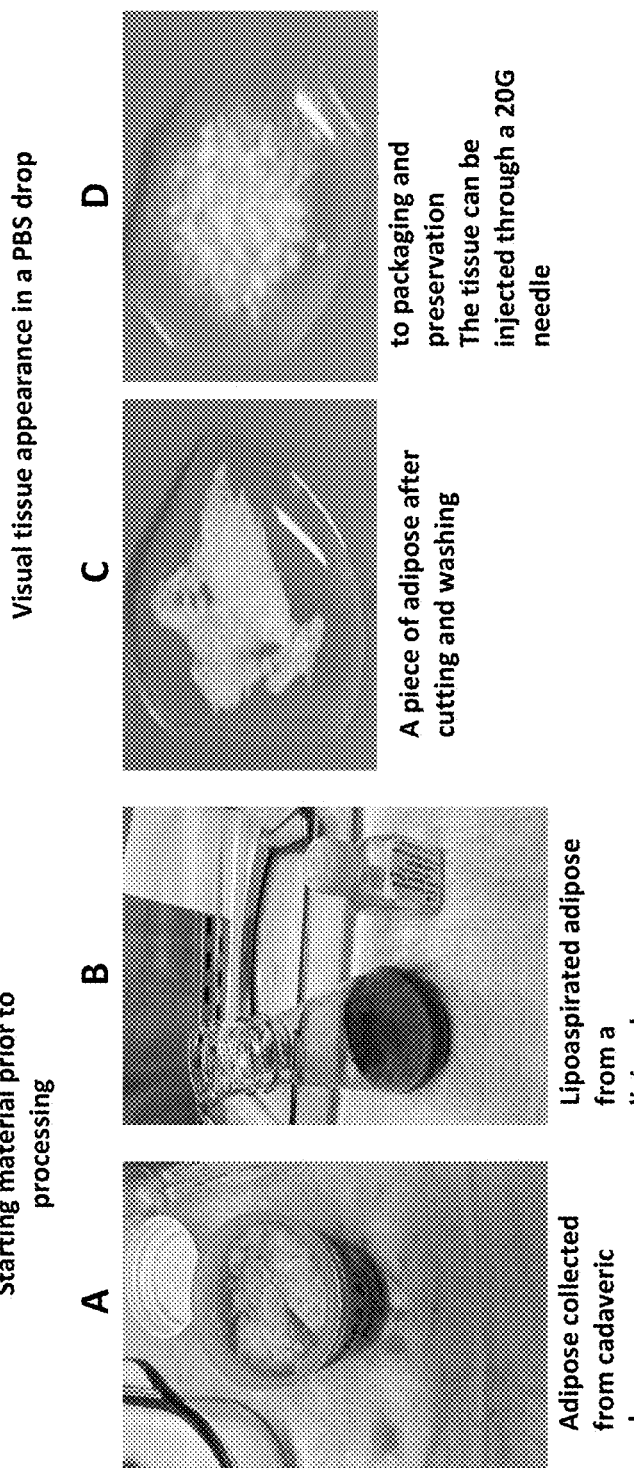
FIGS. 1A-D shows visual appearance of starting material & processed adipose. Starting material prior to processing: adipose collected from cadaveric donor (FIG. 1A) and lipoaspirated adipose from a living donor (FIG. 1B). Visual tissue appearance in a PBS drop: A piece of adipose after cutting and washing (FIG. 1C) and processed adipose prior to packaging and preservation. The tissue can be injected through a 20G needle (FIG. 1D).

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "an adipose tissue" includes a plurality of such adipose tissues, reference to "the adipose tissue" is a reference to one or more adipose tissues and equivalents thereof known to those skilled in the art, and so forth.

As used herein, the term "subject" or "patient" can be used interchangeably and refer to any organism to which a composition of this invention may be administered, e.g., for experimental, diagnostic, and/or therapeutic purposes. Typical subjects include animals (e.g., mammals such as non-human primates, and humans; avians; domestic household or farm animals such as cats, dogs, sheep, goats, cattle, horses and pigs; laboratory animals such as mice, rats and guinea pigs; rabbits; fish; reptiles; zoo and wild animals). Typically, "subjects" are animals, including mammals such as humans and primates; and the like.

By "treat" is meant to administer a devitalized adipose tissue to a subject, such as a human or other mammal (for example, an animal model) that has an increased susceptibility for developing a disease or condition, in order to prevent or delay a worsening of the effects of the disease or condition, or to partially or fully reverse the effects of the disease or condition. For example, "treat" can mean to prevent disease progression.

By "prevent" is meant to minimize the chance that a subject who has an increased susceptibility for developing a disease or disorder will develop the disease or disorder such as fat pad atrophy.

As used herein, the terms "administering" and "administration" refer to any method of providing an adipose tissue or composition as described herein, to a subject. Such methods are well known to those skilled in the art and include, but are not limited to: subcutaneous administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and oral administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In an aspect, the skilled person can determine an efficacious dose, an efficacious schedule, or an efficacious route of administration so as to treat a subject.

By an "effective amount" of a composition as provided herein is meant a sufficient amount of the composition to provide the desired effect. The exact amount required will vary from subject to subject, depending on the species, age, and general condition of the subject, the severity of disease (or underlying genetic defect) that is being treated, the particular composition used, its mode of administration, and the like. Thus, it is not possible to specify an exact "effective amount." However, an appropriate "effective amount" may be determined by one of ordinary skill in the art using only routine experimentation. The term "therapeutically effective amount" means an amount of a therapeutic, prophylactic, and/or diagnostic agent (e.g., adipose tissue) that is sufficient, when administered to a subject suffering from or susceptible to a specific disease or condition (e.g., metabolic diseases, soft-tissue malformation) to treat, alleviate, ameliorate, relieve, alleviate symptoms of, prevent, delay onset of, inhibit progression of, reduce severity of, and/or reduce incidence of the disease or condition.

"Natural", in the context of, for example, "natural adipose tissue," refers to properties exhibited by the adipose tissue in its native state in the subject or donor. Thus, in some aspects, natural adipose tissue and native adipose tissue can be used interchangeably.

As used herein, the term "native" refers to a composition present in a source composition prior to further manipulation. For example, "native viable cells" are the viable cells present in a tissue prior to manipulation or processing of the adipose tissue. In some aspects, native viable cells are the viable cells present in adipose tissue prior to devitalization of the adipose tissue. Similarly, "native adipose tissue factors" refers to adipose tissue factors present in adipose tissue prior to manipulation or processing of the adipose tissue.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents. It will be clearly understood that, although a number of publications are referred to herein, such reference does not constitute an admission that any of these documents form part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Compositions

As described herein, the term composition can be used to refer to a devitalized adipose tissue alone or a devitalized adipose tissue in combination with something else, such as a pharmaceutically acceptable carrier.

Disclosed are devitalized adipose tissue. Disclosed are compositions comprising devitalized adipose tissue. Disclosed are adipose matrices comprising devitalized adipose tissue. In some aspects, the devitalized adipose tissue can be white adipose or brown adipose.

In some aspects, the term "devitalized" means at some point 100% of the native cells (e.g., cells that originated from a tissue) have been killed and at least a portion of the killed cells (i.e., nonviable cells) are present in the tissue. For example, the term "devitalized adipose tissue" refers to an adipose tissue where cells that originated from adipose tissue have been killed and at least a portion of the killed cells (i.e., nonviable cells) are present in the devitalized adipose tissue. In some aspects, a devitalized adipose tissue can later be populated with cells; however, if the adipose tissue was initially devitalized then even after populating with cells at a later step the adipose tissue can still be referred to as devitalized. In some aspects, devitalized adipose tissue can mean that 98% of the cells initially present in the adipose tissue are dead. In some aspects, devitalized adipose tissue can mean that at least 50-98% of the original cells are still present in the tissue even though they are dead. In some aspects, devitalized adipose tissue comprises less than 5% of the native viable cells. In some aspects, the native viable cells are the viable cells present in adipose tissue prior to devitalization. Thus, in some aspects, the devitalized adipose tissue comprises less than 5% of the native viable cells present in the adipose tissue prior to devitalization.

In some aspects, the devitalized adipose tissue comprises at least 90% of the original lipids (i.e., the lipids present in the adipose tissue prior to devitalization). In some aspects, the devitalized adipose tissue comprises at least 70%, 75%, 80%, 85%, 90%, 95%, or 100% of the original lipids. In some aspects, the percent of lipids present in the devitalized adipose tissue is based on the total amount of lipids present in the adipose tissue prior to devitalization.

In some aspects, the devitalized adipose tissue can be minced or micronized. In some aspects, the minced devitalized adipose tissue comprises pieces of devitalized adipose tissue less than 1 mm in size. In some aspects, the minced or micronized devitalized adipose tissue is a homogenous population of pieces of devitalized adipose tissue less than 1 mm in size or less than 2 mm in size. In some aspects, the minced or micronized devitalized adipose tissue is a non-homogenous population of pieces of devitalized adipose tissue less than 1 mm in size or less than 2 mm in size. In some aspects, adipose tissue, before or after devitalization, can be passed through one or more syringes in order to mince the tissue. In some aspects, the syringe can be a 15G, 16G, 17G, 18G, 20G, 21G, 22G, 23G, 24G, or 25G needle. Thus, the minced adipose tissue can be a range of sizes depending on the inner diameter of the needle. In some aspects, the width of the pieces of minced adipose tissue is less than 1 mm or less than 2 mm. In some aspects, the length of the pieces of minced adipose tissue can be longer than the width.

In some aspects, the devitalized adipose tissue comprises all of the components of native adipose tissue except for a portion of the lipids and some cells. In some aspects, the devitalized adipose tissue comprises native adipose tissue factors. In some aspects, the native adipose tissue factors that can provide therapeutic effects include, but are not limited to, adiponectin, leptin, vascular endothelial growth factors (VEGFs), platelet-derived growth (PDGFs), fibroblast growth Factors (FGFs), IL-6, IL-8, insulin like growth factors (IGFs), and hepatocyte growth factor (HGF). In some aspects, the devitalized adipose tissue comprises at least 50, 60, 70, 80, 90, or 95% of the native growth factors.

In some aspects, the devitalized adipose tissue comprises all of the components of native adipose tissue. Thus, in some aspects, the devitalized adipose tissue retains its native structure. In some aspects, the native structure of devitalized adipose tissue is a loose connective tissue comprising collagen fibers and blood vessels. In some aspects the native structure of adipose tissue comprises adipocytes and fibroblasts. In some aspects, the devitalized adipose tissue can comprise dead adipocytes and fibroblasts.

In some aspects, the devitalized adipose tissue is not decellularized. In some aspects, "decellularized" can refer to 100%, 95%, 90%, 85%, 80%, 75%, or 70% of the cells (alive or dead) being removed from the adipose tissue. Thus, devitalized adipose tissue that is not decellularized means the devitalized adipose tissue retains 100%, 95%, 90%, 85%, 80%, 75%, 70%, 65%, 60%, 55% or 50% of the cells present in the adipose tissue prior to devitalization.

In some aspects, the devitalized adipose tissue can comprise less than 20%, 15%, 10%, 5%, 2%, 1%, 0.5%, 0.2%, 0.1%, 0.05% or 0.01% peroxidized lipids of the total lipids. In an aspect, the percent peroxidized lipids of the total lipids can be calculated by taking into consideration that adipose tissue has approximately 80-98% lipids for which 90% of the lipids are triglycerides. In some aspects, for purposes of a calculation, the molecular weight of the triglycerides can be approximately 176-200 ng. 200 ng is approximately 1 nmol. In some aspects, 0.8-0.98 mg of fat is in 1 mg of adipose which would be approximately 4000-5000 nmol/mg of adipose tissue. Thus based on these assumptions, in some aspects, ~9 nmol/mg of tissue peroxidized lipids would equate to ~0.1-0.2% peroxidized lipids of the total lipids. In some aspects, the presence of peroxidized lipids can result in increased inflammation. Thus, identifying devitalized adipose tissue having a low percentage of peroxidized lipids can be used in producing the best adipose graft. In some aspects, the levels of peroxidized lipids can be measured via a colorimetric TBAR method. In some aspects, the peroxidized lipids can be measured by a colorimetic TBAR method.

In some aspects, the disclosed adipose tissue is not radiated. In some aspects, the disclosed adipose tissue is radiated in an amount of less than 15 kGy. In some aspects, radiation can affect the amount of peroxidized lipids.

1. Pharmaceutical Compositions

Disclosed are pharmaceutical compositions comprising any of the adipose matrices, adipose tissues, or compositions disclosed herein and a pharmaceutically acceptable carrier. For example, disclosed are pharmaceutical compositions comprising a composition comprising a devitalized adipose tissue and a pharmaceutically acceptable carrier.

Disclosed herein are pharmaceutical compositions that comprise one or more of the compositions disclosed herein. In an aspect, the pharmaceutical composition can comprise any of the devitalized adipose tissues disclosed herein.

In some aspects, the pharmaceutical compositions can further comprise a pharmaceutically acceptable carrier. In some aspects, the pharmaceutical compositions described herein can be sterile and contain any of the disclosed compositions for producing the desired response in a unit of weight or volume suitable for administration to a subject. In some aspects, the pharmaceutical compositions can contain suitable buffering agents, including, e.g., acetic acid in a salt; citric acid in a salt; boric acid in a salt; and phosphoric acid in a salt.

When administered, the disclosed compositions or pharmaceutical compositions can be administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents.

As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term denotes an organic or inorganic ingredient, natural or synthetic, with which the active ingredient is combined to facilitate the application. The components of the pharmaceutical compositions also are capable of being co-mingled with the disclosed compositions, and with each other, in a manner such that there is no interaction which would substantially impair the desired pharmaceutical efficacy.

As used herein, the term "pharmaceutically acceptable carrier" refers to solvents, dispersion media, coatings, antibacterial, isotonic and absorption delaying agents, buffers, excipients, binders, lubricants, gels, surfactants that can be used as media for a pharmaceutically acceptable substance. The pharmaceutically acceptable carriers can be lipid-based or a polymer-based colloid. Examples of colloids include liposomes, hydrogels, microparticles, nanoparticles and micelles. The compositions can be formulated for administration by any of a variety of routes of administration, and can include one or more physiologically acceptable excipients, which can vary depending on the route of administration. Any of the compositions described herein can be administered in the form of a pharmaceutical composition.

As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed. The compositions can also include additional agents (e.g., preservatives).

The pharmaceutical compositions disclosed herein can be sterile and sterilized by conventional sterilization techniques developed for non-soluble biological material like collagens. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment. The compositions can also be formulated as powders, elixirs, suspensions, emulsions, solutions, syrups, aerosols, lotions, creams, ointments, gels, suppositories, sterile injectable solutions and sterile packaged powders. The active ingredient can be any of the adipose or devitalized adipose tissues described herein in combination with one or more pharmaceutically acceptable carriers. As used herein "pharmaceutically acceptable" means molecules and compositions that do not produce or lead to an untoward reaction (i.e., adverse, negative or allergic reaction) when administered to a subject as intended (i.e., as appropriate).

In some aspects, administration of disclosed compositions or pharmaceutical compositions disclosed herein can be administered to mammals other than humans, e.g., for testing purposes or veterinary therapeutic purposes, can be carried out under substantially the same conditions as described above.

2. Cryopreserved or Lyophilized Compositions

In some aspects, the disclosed devitalized adipose tissues can be cryopreserved. In some aspects, the disclosed devitalized adipose tissues can further comprise a cryopreservation solution. In some aspects, the disclosed devitalized adipose tissues can be previously cryopreserved. In some aspects, the disclosed compositions or pharmaceutical compositions can be cryopreserved. In some aspects, the disclosed compositions or pharmaceutical compositions can further comprise a cryopreservation solution. In some aspects, the disclosed compositions or pharmaceutical compositions can be previously cryopreserved. "Previously cryopreserved" can mean a composition that was once cryopreserved but has been removed (e.g., thawed) from the cryopreserved state.

Thus, for example, disclosed are compositions comprising a devitalized adipose tissue as described herein and further comprising a cryopreservation solution.

Disclosed herein are adipose matrices comprising a devitalized adipose tissue as described herein. Disclosed herein are cryopreserved compositions comprising an adipose matrix comprising devitalized adipose tissue as described herein.

In some aspects, the cryopreserved adipose tissues, adipose matrices and/or compositions comprising cryopreserved adipose tissues comprise at least 50% native lipids. In some aspects, the cryopreserved adipose tissue, matrix or composition, when thawed, can comprise at least 50% lipids. In some aspects, the cryopreserved or previously cryopreserved adipose tissues, adipose matrices or compositions can comprise greater than 70, 75, 80, 85, 90, 95, or 99% lipids. In some aspects, the cryopreserved or previously cryopreserved adipose tissues, adipose matrices or compositions can comprise less than 55, 70, 75, 80, 85, 90, 95, or 99% lipids. The percent of lipids present after thawing is at least 50, 60, 70, 80, 90, or 100% of the lipids present immediately prior to cryopreservation. In some aspects, free lipids can be removed from the devitalized adipose tissue. In some aspects, removing at least 5, 10, 15, 20, 25, 30, 35, 40, 45, or 50% of free lipids can help with lyophilization.

In some aspects, the cryopreserved or previously cryopreserved adipose tissue, adipose matrix or composition can be cut to a desired size. In some aspects, the adipose tissue can be minced or micronized to suitable sizes as described above.

In some aspects, a cryopreservation solution can contain one or more non-cell permeating cryopreservatives. Examples of non-cell permeating cryopreservatives, include but not limited to, polyvinyl pyrrolidone, a hydroxyethyl starch, a polysaccharide, a monosaccharide, an alginate, trehalose, raffinose, dextran, human serum albumin, Ficoll, lipoproteins, polyvinyl pyrrolidone, hydroxyethyl starch, autologous plasma or a mixture thereof. In some aspects, the cryopreservative does not contain DMSO or glycerol. Further, a cryopreservation solution can contain serum albumin or other suitable proteins to stabilize the disclosed compositions during the freeze-thaw process and to reduce the damage to cells, thereby maintaining viability. In some aspects, a cryopreservation solution can contain a physiological solution, such as a physiological buffer or saline, for example phosphate buffer saline. In some aspects, a cryopreservation solution can comprise a lyoprotectant, such as trehalose or trehalose in combination with one or more antioxidants.

In some aspects, the disclosed compositions can be lyophilized.

Disclosed are lyophilized devitalized adipose tissues. Disclosed are lyophilized adipose matrices comprising devitalized adipose tissue. Disclosed are lyophilized compositions comprising a devitalized adipose tissue.

In some aspects, the disclosed lyophilized adipose tissues, adipose matrices or compositions comprise less than 15% residual water. In some aspects, the disclosed lyophilized adipose tissues, adipose matrices or compositions comprise 5-12% residual water. In some aspects, the disclosed lyophilized adipose tissues, adipose matrices or compositions comprise ≤10% residual water. In some aspects, the disclosed lyophilized adipose tissues, adipose matrices or compositions comprise ≤5% residual water. In some aspects, the disclosed lyophilized adipose tissues, adipose matrices or compositions comprise ≤5%, 4%, 3%, 2%, or 1% residual water. In some aspects, the disclosed lyophilized adipose tissues, adipose matrices or compositions comprise 6.65+/− 1.61% residual water.

In some aspects, the disclosed lyophilized adipose tissues, adipose matrices or compositions comprise trehalose. In some aspects, the disclosed lyophilized adipose tissues, adipose matrices or compositions comprise trehalose, wherein the trehalose is present at a concentration of 0.1M-1.5M.

In some aspects, the lyophilized adipose tissues, adipose matrices or compositions disclosed herein can be stable for at least three weeks. In some aspects, the lyophilized adipose tissues, adipose matrices or compositions can be stable for at least three months. In some aspects, the lyophilized compositions can be stable for 1, 2, 3, 4, 5, 6, 7, 8, 9, 10, 11, 12, 24, 36, 48, or 60 months.

In some aspects, the lyophilized compositions disclosed herein can be reconstituted resulting in a reconstituted tissue. The described lyophilized adipose tissues, adipose matrices or compositions can be reconstituted using standard techniques known in the art. In some aspects, reconstituting refers to rehydrating. Thus, the disclosed lyophilized adipose tissues, adipose matrices or compositions can be reconstituted or rehydrated using water, saline, a buffer such as, but not limited to phosphate buffered saline (PBS), in a solution comprising a stabilizing agent such as, but not limited to bovine serum albumin (BSA), Plasma-Lyte A or other clinically available electrolyte solutions, with human bodily fluids or a combination thereof. For example, lyophilized adipose tissues, adipose matrices or compositions can be applied directly to a wound on a subject and the subject's bodily fluids can reconstitute. In some aspects, a combination of bodily fluids and another known rehydrating solution can be used.

C. Methods of Use

Any of the disclosed methods can be performed by administering one or more of the compositions disclosed herein. For example, disclosed are methods comprising administering a composition comprising a devitalized adipose tissue as disclosed herein.

In some aspects, the composition comprising devitalized adipose tissue can be administered subcutaneously. In some aspects, the composition comprising devitalized adipose tissue can be administered in subcutaneous adipose. In some aspects, the composition comprising devitalized adipose tissue can be administered directly to an area of soft tissue defect, such as an area resulting from trauma, tumor removal, or congenital defects. In some aspects, the composition comprising devitalized adipose tissue can be administered underneath a wound bed or in the area of scar tissue. In some aspects, the composition comprising devitalized adipose tissue can be administered into joint space or intraarticularly.

In some aspects, a therapeutically effective amount of the disclosed adipose tissues or compositions can be administered for any of the disclosed methods.

1. Methods of Augmenting Soft Tissue

Disclosed are methods of augmenting a soft tissue site of a subject in need thereof comprising administering to the subject one or more of the compositions disclosed herein. For example, disclosed are methods of augmenting a soft tissue site of a subject in need thereof comprising administering to the subject a composition comprising devitalized adipose tissue.

In some aspects, a soft tissue site for augmentation includes, but is not limited to, the face, the buttocks, depressed scar contours, tissue atrophy related to aging, scarring, radiation or disease, or any body deformity or area that is desirable for augmentation. In some aspects, one or both breasts subjected to a partial or total mastectomy, biopsy, or other disfiguring event can be augmented in order to restore physiological symmetry and psychological well-being. In some aspects, correction of natural abnormalities such as scarring and dimpling can be soft tissue sites for augmentation. Still, in other instances, the breasts can be augmented to improve cosmetics and self-esteem.

In some aspects, a subject in need thereof is a subject that has a soft tissue site that could benefit from augmentation. Thus, in some aspects, a subject in need thereof can be a subject having, but not limited to, a scar, a wound, wrinkles, lipodystrophy, resected tumor, or congenital soft tissue defect. In some aspects, a subject having a wound can be a subject having a burn.

The disclosed methods of augmenting a soft tissue site of a subject in need thereof can also be understood to be methods of fat transplantation or fat grafting to a target site of a subject in need thereof. Thus, disclosed are methods of fat transplantation or fat grafting to a target site of a subject in need thereof comprising administering to the subject one or more of the compositions disclosed herein. For example, disclosed are methods of fat transplantation or fat grafting to a target site of a subject in need thereof comprising administering to the subject a composition comprising devitalized adipose tissue.

In some aspects, the fat transplantation or fat grafting disclosed herein can be used for, but is not limited to, reconstructive breast surgery, filling atrophic, hypertrophic or keloid scars, reducing scar contracture, filling burn scars, filling lipodystrophy, correcting soft-tissue deficiencies, and aesthetic/cosmetic procedures. Aesthetic/cosmetic procedures can include, but are not limited to, facial rejuvenation, hand rejuvenation, rhinoplasty, breast augmentation/symmetry, or gluteal augmentation.

In some aspects of the methods of augmenting or methods of fat transplantation/grafting, the adipose tissue provides a wound healing therapeutic effect. In some aspects, the wound healing therapeutic effect repairs burned tissue. In some aspects, the wound healing therapeutic effect provides volume and cushioning to the wound. In some aspects, the wound healing therapeutic effect repairs scars and/or burns. In some aspects, the wound healing therapeutic effect corrects a metabolic process via the presence of adipokines and other adipose-specific hormones. In some aspects, the wound healing therapeutic effect can provide angiogenic effects.

In some aspects of the methods of augmenting or methods of fat transplantation/grafting, the adipose tissue provides a cosmetic effect. In some aspects, the cosmetic effect is adding volume to an area of the subject's body. In some aspects, the area of the subject's body can be, but is not limited to, the face, breasts, hips, buttocks, hands or feet. In some aspects, the cosmetic effect improves the texture and appearance of the skin. For example, the cosmetic effect can be reducing wrinkles or dimples in the skin.

In some aspects of the disclosed methods, the adipose tissue used to produce devitalized adipose tissue is derived from the adipose of the subject in need thereof who is being administered the composition comprising devitalized adipose tissue. Thus, the devitalized adipose tissue can be autologous to the subject receiving the devitalized adipose tissue.

In some aspects of the disclosed methods, the adipose tissue used to produce devitalized adipose tissue is derived from the adipose of a subject different from the subject in need thereof who is being administered the composition comprising devitalized adipose tissue. Thus, the devitalized adipose tissue can be allogenic. In some aspects, the devitalized adipose tissue can be from a subject other than the subject receiving the devitalized adipose tissue. In some aspects, a subject different from the subject in need thereof can be a cadaver. Thus, in some aspects, the devitalized adipose tissue can be derived from a cadaver.

In some aspects, the devitalized adipose tissue is infiltrated with macrophages and/or mesenchymal stem cells (MSCs) derived from the subject after the subject is administered with the composition comprising devitalized adipose tissue.

In some aspects, new blood vessels are formed in the devitalized adipose tissue after administration to the subject. The devitalized adipose tissue can contain biological factors (like growth factors, adipokines and cytokines) which have angiogenic activity leading to new blood vessel formation. In some aspects, angiogenic growth factors present in the disclosed adipose tissues and compositions can attract endothelial cells. Also, M2 macrophages can be pro-angiogenic as they secrete growth factors to stimulate new blood vessel formation. Thus, in some aspects, the M2 macrophages populate the injected adipose tissues or compositions and induce blood vessel formation.

In some aspects of any of the disclosed methods, the composition can be administered subcutaneously. For example, subcutaneously can include administering in the subcutaneous fat. In some aspects, the composition can be administered using any known technique for administering therapeutics to a subject. In some aspects, the composition can be administered using any of the routes of administration described herein.

In some aspects, augmenting soft tissue with one or more of the devitalized tissues, adipose matrix or composition comprising the devitalized adipose tissue disclosed herein results in a cushioning effect.

In some aspects of any of the disclosed methods, the devitalized tissues, adipose matrix or composition comprising the devitalized adipose tissue can be any of those described herein.

2. Methods of Treating

Disclosed are methods of treating a subject having fat pad atrophy comprising administering to the subject one or more of the compositions disclosed herein. For example, disclosed are methods of treating a subject having fat pad atrophy comprising administering to the subject a composition comprising devitalized adipose tissue.

In some aspects, fat pad atrophy is characterized by gradual thinning of the fat pad on the bottom of the foot. This condition can cause severe pain and discomfort. Fat pad atrophy can develop as a result of an injury that has occurred, or from medical conditions such as diabetes and arthritis. Thus, a treatment for fat pad atrophy is beneficial.

Disclosed are methods of treating a subject having lipo-dystrophy comprising administering to the subject one or more of the compositions disclosed herein. For example, disclosed are methods of treating a subject having lipodys-trophy comprising administering to the subject a composition comprising devitalized adipose tissue. In some aspects, the lipodystrophy is HIV-associated lipoatrophy. Anti-retro-viral therapy (ART) can result in the redistribution of adipose tissue. Therefore, a subject having lipodystrophy can be a subject on ARTs.

Disclosed are methods of treating a subject having a metabolic disease or condition comprising administering to the subject one or more of the compositions disclosed herein. For example, disclosed are methods of treating a subject having a metabolic disease or condition comprising administering to the subject a composition comprising devi-talized adipose tissue. In some aspects, the metabolic disease or condition can be, but is not limited to, dyslipidemia/hyperlipidemia (for example, subjects with high choles-terol), metabolic syndrome, obesity, type 2 diabetes, insulin resistance, or lipodystrophy.

In some aspects of the disclosed methods, the adipose tissue used to produce devitalized adipose tissue is derived from the adipose of the subject who is being administered the composition comprising devitalized adipose tissue. Thus, the devitalized adipose tissue can be autologous to the subject receiving the devitalized adipose tissue.

In some aspects of the disclosed methods, the adipose tissue used to produce devitalized adipose tissue is derived from the adipose of a subject different from the subject who is being administered the composition comprising devital-ized adipose tissue. Thus, the devitalized adipose tissue can be allogeneic to the subject receiving the devitalized adipose tissue. In some aspects, a subject different from the subject being administered the composition comprising devitalized adipose tissue can be a cadaver. Thus, in some aspects, the adipose tissue is derived from a cadaver.

In some aspects of the disclosed methods of treating provide a therapeutic effect that can provide volume and cushioning to a site of injection. For example, volume and cushioning can be provided to the fat pad. In some aspects, the therapeutic effect corrects a metabolic process via the presence of adipokines and other adipose-specific hormones. In some aspects, the therapeutic effect can provide angio-genic effects.

In some aspects of any of the disclosed methods, the composition can be administered subcutaneously. For example, subcutaneously can include administering in the subcutaneous fat. In some aspects, the composition can be administered using any known technique for administering therapeutics to a subject. In some aspects, the composition can be administered using any of the routes of administra-tion described herein.

In some aspects of any of the disclosed methods, the devitalized tissues, adipose matrix or composition compris-ing the devitalized adipose tissue can be any of the devital-ized adipose tissues described herein.

In some aspects, the devitalized adipose tissue is infil-trated with macrophages and/or mesenchymal stem cells (MSCs) derived from the subject after the subject is admin-istered with the composition comprising devitalized adipose tissue.

In some aspects, new blood vessels are formed in the devitalized adipose tissue after administration to the subject. The devitalized adipose tissue contains biological factors (like growth factors, adipokines and cytokines) which have angiogenic activity leading to new blood vessel formation. In some aspects, angiogenic growth factors present in the disclosed adipose tissues and compositions can attract endothelial cells. Also, M2 macrophages can be pro-angio-genic as they secrete growth factors to stimulate new blood vessel formation. Thus, in some aspects, the M2 macro-phages populate the injected adipose tissues or compositions and induce blood vessel formation.

Disclosed are methods of treating a subject having foot ulcerations comprising administering to the subject one or more of the compositions disclosed herein. For example, disclosed are methods of treating a subject having foot ulcerations comprising administering to the subject a com-position comprising devitalized adipose tissue. In some aspects, treating includes preventing from occurring or pre-venting from worsening. Thus, disclosed are methods of preventing foot ulcerations or preventing a worsening of foot ulcerations comprising administering to the subject a composition comprising devitalized adipose tissue.

In some aspects, the composition comprising devitalized adipose tissue provides a cushioning effect that can prevent foot ulcerations by offloading the pressure point.

In some aspects, prior to treating with a devitalized adipose tissue, the devitalized adipose tissue is first analyzed for the amount of peroxidized lipids present in the devital-ized adipose tissue. Higher levels of peroxidized lipids can result in negative effects of the adipose tissue in a subject. Thus, in some aspects, devitalized adipose tissue having higher than 2%, 5%, 10%, or 15% peroxidized lipids are not used in the disclosed treatments.

3. Delivery of Compositions

The disclosed adipose tissues, devitalized adipose tissues, adipose matrices and compositions comprising the adipose tissues can be delivered using a variety of well-known techniques.

Preparations of parenteral administration include sterile aqueous or non-aqueous solutions, suspensions, and emul-sions. Examples of non-aqueous solvents are propylene glycol, polyethylene glycol, vegetable oils such as olive oil, and injectable organic esters such as ethyl oleate. Aqueous carriers include water, alcoholic/aqueous solutions, emul-sions or suspensions, including saline and buffered media. Parenteral vehicles include sodium chloride solution, Ring-er's dextrose, dextrose and sodium chloride, lactated Ring-er's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

D. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example, disclosed are kits comprising one or more of the adipose tissues or compositions as described herein. The kits also can contain instructions for making the disclosed compositions.

In some aspects, the kits can further comprise cryopreservatives or lyopreservatives.

EXAMPLES

A. Example 1. Viable Cryopreserved and Non-Viable Lyophilized Human Adipose Tissue Product Processing, Packaging and Preservation Human adipose tissues were received from eligible adult living and cadaveric donors after obtaining written informed consent, and tissue regulations for receipt and disposition of tissues was strictly followed.

Cutting: Adipose tissue from cadaveric donors was cut using scissors and scalpel into small (3-5 mm) pieces. Adipose tissue from lipoaspirate obtained from living donors was already in ~3 mm pieces and does not require cutting.

Washing: Pieces of cut adipose tissue were washed with 10× volume of saline or PBS. Optionally, tissue can be washed with a solution of ACD-A or another anti-coagulant to prevent any further blood clotting. Optionally, antibiotics can be added to the wash solution.

Micronization: Washed adipose was micronized using a "mezzaluna" knife until the tissue was becoming a homogeneous mass with <1 mm tissue particle size. During this step fibrous pieces were removed.

Filtration: Micronized tissue was filtered through 1 mm nylon filter, and then, through 0.75 mm nylon filter.

Removal of free lipids (optional step): Micronized filtered tissue was incubated overnight in PBS at 37° C. on a rotator to separate free lipids released from cells during tissue micronization and filtration. Optionally, antibiotics can be added to PBS. Free lipids form a separate layer on the top of the tissue. This layer was removed with a pipette.

Preparation for preservation: micronized filtered adipose was mixed 1:1 (V/V) with a preservation solution (0.1-1.5 M trehalose in PBS, or 5-10% DMSO alone or in combination with trehalose and/or albumin or fetal bovine serum) and incubated at room temperature for 15-60 min with periodical mixing the tissue in the preservation solution. After incubation the preservation solution was decanted, and the adipose tissue was aliquoted in glass vials or syringes.

Freezing: Vials and syringes with aliquoted adipose were placed at −80° C. prior to the use.

Lyophilization: Glass vials with frozen adipose were placed on a pre-chilled to −45° C. shelf in a lyophilizer. Samples were dried for 48 h using a one-step program with gradual temperature increase from −45° C. to +18° C. When the drying was complete vials were sealed under vacuum in the lyophilizer. Lyophilization protocols with 24 and 72 h one-step drying were also tested. The vials with freeze-dried adipose were stored at room temperature prior to the use.

Terminal sterilization: Optionally, vials with freeze-dried adipose can be sterilized using gamma or E-beam radiation.

Thawing and rehydration of cryopreserved and lyophilized adipose tissue products: Syringes or vials with cryopreserved adipose were placed in 37° C. water bath for 3-15 min depending on the volume of the tissue. Vials with lyophilized adipose were reconstituted by adding to the vial 1:1 (V/V) solution. Several solutions were tested including water, saline, PBS and DMEM medium with and without albumin or fetal bovine serum (FBS).

Devitalized cryopreserved human adipose tissue: To create devitalized human adipose, samples of processed tissues were subjected to 5 cycles of freeze-thaw using dry ice. The lack of viable cells in the tissue was confirmed by Calcein/PI staining and by the ATP metabolic assay. Devitalized tissue was cryopreserved in DMSO as described herein.

In total, 13 adipose tissue donors were processed: 5 cadaveric and 8 living donors. Donors characteristics are presented in tables 1 and 2. Living donors were all females and younger than cadaveric donors; however, the average BMI was similar for both groups of donors.

FIG. 1 shows visual appearance of adipose derived from cadaveric (FIG. 1A) and adipose derived from living donors (FIG. 1B), one piece of adipose after cutting and washing (FIG. 1C), and the processed adipose prior to packaging and preservation (FIG. 1D). The processed adipose can be injected via 20G needles.

Table 1 shows cadaveric adipose tissue donor's characteristics

| Characteristics | Cadaveric Donor # | | | | | Mean +/− |
| | 1 | 2 | 3 | 4 | 5 | SD or % |
| --- | --- | --- | --- | --- | --- | --- |
| Age (years) | 81 | 47 | 63 | 61 | 58 | 62 +/− 12.19 |
| Gender | F | M | M | M | F | 60% M/40% F |
| BMI | 29.95 | 37.52 | 25.38 | 34.3 | 25.83 | 30.6 +/− 5.29 |
| Race | Caucasian | Caucasian | Caucasian | Caucasian | Caucasian | 100% Caucasian |
| Cause of death | Anoxia | Cardiac arrest | Cardiac arrest | Cardiopulmonary arrest | Anoxia | |
| Tissue recovery interval (hours) | 7.5 | Not provided | 12.7 | 8.9 | 13 | 10.53 +/− 2.75 |

Table 2 shows living adipose tissue donor's characteristics

| Characteristics | Living Donor # | | | | | | | | Mean +/− SD or % |
|---|---|---|---|---|---|---|---|---|---|
| | 1 | 2 | 3 | 4 | 5 | 6 | 7 | 8 | |
| Age (years) | 37 | 51 | 46 | 63 | 65 | 59 | 42 | 36 | 49.88 +/− 11.47 |
| Gender | F | F | F | F | F | F | F | F | 100% F |
| BMI | 23 | 29.7 | 34.3 | 36.8 | 34.2 | 24.5 | 27.8 | 35.6 | 30.74 +/− 5.26 |
| Race | Caucasian | Caucasian | African-American | Caucasian | Caucasian | Caucasian | Caucasian | African American | 75% Caucasian/25% African-American |

B. Example 2. Confirmation of the Presence of Viable Cells in the Viable Cryopreserved Human Adipose Tissue Product Cell viability: Cell viability of cryopreserved post-thaw adipose tissue was evaluated microscopically after staining the tissues with Calcein/Propidium Iodine (PI) or Acridine Orange (AO)/PI fluorescent dyes or by using the ATP metabolic assay according to the standard protocols. Around 50 µL of adipose tissue samples were mixed with 50 µL of AO/PI or Calcein/PI. Microscopic evaluation of AO/PI and Calcein/PI-stained tissues was performed after 5 min and 20 min of staining at room temperature (RT), respectively. For the ATP assay, samples (50 µL/well) in 96-well plates were mixed with 50 µL/well DMEM-10% FBS and 100 µL/well the CellTiter-Glo 2.0 assay reagent. The plate was incubated for 20 min at RT in dark place followed by the plate reading using a Luminometer.

The presence of viable adipocytes and stromal vascular fraction (SVF) cells isolated from the tissue was evaluated by the ATP assay and AO/PI staining, respectively. The attachment and growth of the SVF cells isolated from the adipose tissues in the cell culture plates/flasks served as an additional confirmation of the presence of viable functional cells in the viable cryopreserved human adipose tissue product.

SVF cell isolation: Fresh, post-thaw and rehydrated adipose was digested to isolate SVF cells. Five-six mL of tissue were placed in a 15 mL tube in 5 mL of DMEM-10% FBS and 0.25 mL 2% collagenase type 2. The tube was incubated at 37° C. for 45 min on a rotator. After that digested tissue was filtered via a 300 µm nylon filter and transferred into 15 mL tubes. Digested tissue was centrifuged 5 min at 1200 rpm. Top layer of mature adipocytes was collected, and supernatant (SN) was removed. Viability of mature adipocytes was evaluated using the ATP assay. The SVF cell pellet was resuspended in 0.5 mL DMEM-10% FBS. Cell count and viability were performed for SVF cells using AO/PI staining. Cells were plated in a tissue culture plate or a flask in DMEM-10% FBS. Cell attachment and growth were observed microscopically.

Figure 2:
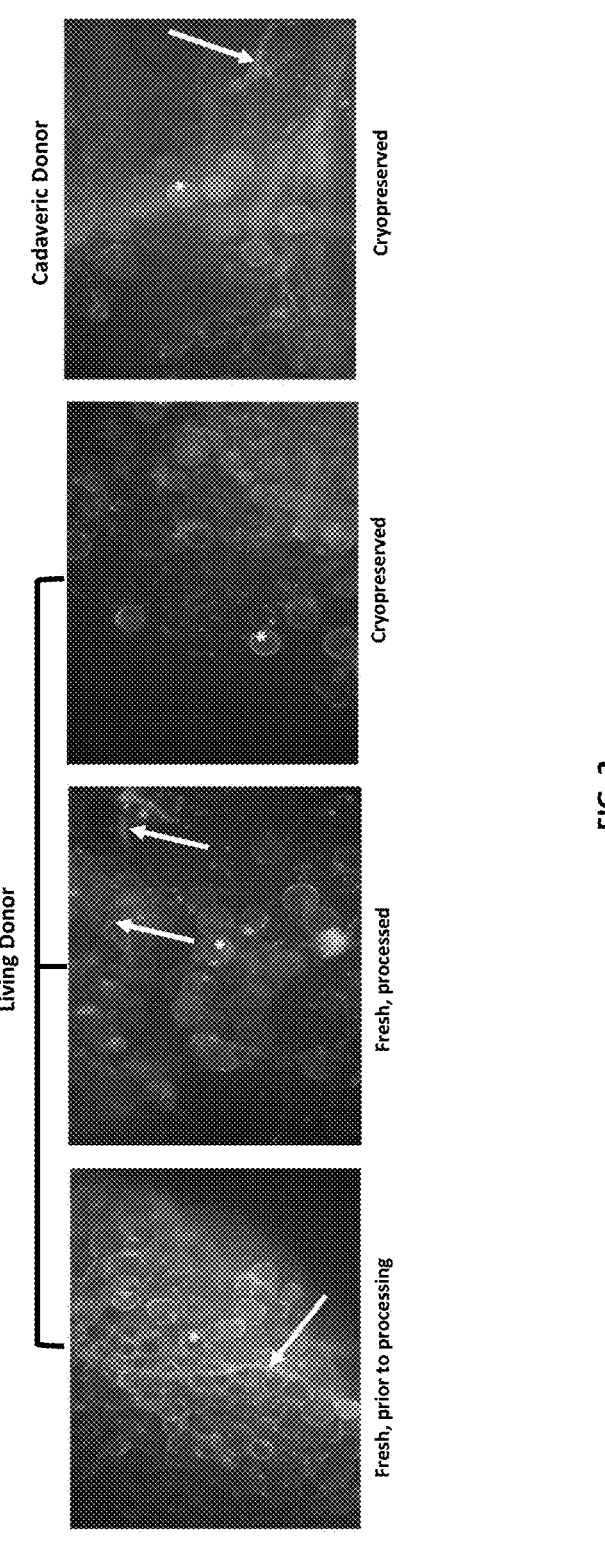
FIG. 2 shows presence of viable cells in the adipose tissue at different steps of the processing confirmed by LIVE/DEAD fluorescent staining. Calcein/PI-stained human adipose tissue: prior to processing, processed and processed cryopreserved. White arrows: blood vessels with viable (green) stromal vascular cells; White stars: viable adipocytes.

Tissue and cell viability for 4 cadaveric and 5 living donors, for which both tissues and isolated cells were tested, are summarized in table 3. The adipose tissue before the processing, the processed fresh and cryopreserved adipose, adipocytes and SVF cells isolated from fresh and cryopreserved tissues from all donors were viable. The adipose collected from living donors usually showed higher metabolic activity (=more viable cells) as compared to the adipose collected from cadaveric donors. Lower viability of adipose from cadaveric donors is due to dead adipocytes, which are highly sensitive to hypoxia and stress; however, there were no significant differences in viability of SVF cells between cadaveric and living donors (Table 3). Two steps in the tissue processing and preservation, tissue micronization and cryopreservation, decrease tissue viability (Table 3, FIG. 2). The decrease in cell viability is linked mostly to adipocyte's death during tissue micronization. The SFV cells remains viable. The SVF cells are a heterogeneous population containing fibroblasts, mesenchymal stem cells, endothelial cells and immune cells; however, after plating of SVF cells in the tissue culture medium, only fibroblast-like cells were growing (FIG. 3).

Table 3 shows presence of viable cells in human adipose tissue samples. *ATP assay data in RLUs (relative luminescent units); % of SVF cell viability was determined by using an automated cell counter of AO/PI-stained samples

| Sample* | Cadaveric donors | | | | | Living donors | | | | | |
|---|---|---|---|---|---|---|---|---|---|---|---|
| | #2 | #3 | #4 | #5 | Mean +/− SD | #1 | #2 | #3 | #4 | #5 | Mean +/− SD |
| Adipose prior to processing | Not tested | 7406 | 9265 | 5825 | 7499 +/− 1406 | 48679 | 49003 | 7294 | 59086 | 17783 | 36369 +/− 20090 |
| Processed adipose, 50 mL | 6848 | 6440 | 4316 | 5513 | 5779 +/− 973 | 16329 | 5866 | 5760 | 29712 | 12386 | 14011 +/− 8820 |
| Cryopreserved processed adipose, 50 mL | 1682 | 6064 | 5681 | 10013 | 5860 +/− 2949 | 4880 | 6746 | 2432 | 19000 | 22326 | 11077 +/− 8015 |
| Adipocytes from fresh tissue, 50 mL of isolated from 5-6 mL tissues | | 4836 | 2451 | 4907 | 4065 +/− 1141 | 82894 | 10140 | 6314 | 59775 | Not tested | 39781 +/− 37670 |
| Adipocytes from cryopreserved tissue, 50 mL of isolated from 5-6 mL tissues | 2484 | 2992 | Not tested | Not tested | 2738 +/− 359 | 11097 | Not tested | Not tested | Not tested | Not tested | 11097 +/− 0 |

-continued

| Sample* | Cadaveric donors | | | | | Living donors | | | | | |
|---|---|---|---|---|---|---|---|---|---|---|---|
| | #2 | #3 | #4 | #5 | Mean +/– SD | #1 | #2 | #3 | #4 | #5 | Mean +/– SD |
| SVF cells from fresh tissue, isolated from 5-6 mL tissues | | 73.8% | 29.8% | 36.6% | 47 +/– 24% | 52.4% | 28% | 70.4% | 77.3% | 75.9% | 61 +/– 19% |
| SVF cells from cryo-preserved tissue, isolated from 5-6 mL tissues | 65% | 34.1% | | 53.1% | 51 +/– 16% | 39% | 45.8% | 40.3% | 57% | 40.5% | 45 +/– 7% |

Table 4 shows results of different cryopreservation solutions on post-thaw adipose tissue viability. Data conclude that to retain tissue viability, the cryopreservation solution must have DMSO. The best solution is 10% DMSO. Other solutions containing DMSO also provide protection for viable cells; however, viability was reduced in comparison to only DMSO-containing solution (Table 4). Trehalose alone had no protective effect for viable cells. There were no differences in cell viability between cryopreserved tissues packaged in glass vials or plastic syringes (data not shown).

Table 4 shows effect of cryopreservation solutions on post-thaw cell viability of adipose tissue

| Cryopreservation solutions | Cadaveric donors | | | | SVF cell outgrowth |
|---|---|---|---|---|---|
| | #1, exp 1 | #1, exp 2 | #2 | #4 | |
| DMEM | 2854 | 1621 | 847 | 427 | No |
| 10% DMSO | 38935 | 11595 | 4500 | 1449 | Yes |
| 0.5M Trehalose | 2715 | 1833 | | 598 | No |
| 0.5M Trehalose-10% DMSO | Not tested | Not tested | 2046 | Not tested | Not tested |
| 0.3M trehalose-5% DMSO | 21704 | 3702 | Not tested | 1193 | Yes |
| 0.2M trehalose-10% DMSO | Not tested | Not tested | Not tested | 1207 | No |

There were no viable cells detected in devitalized cryopreserved and lyophilized adipose tissue by 3 methods: fluorescent staining for live and dead cells, ATP detection, and attachment and growth of isolated SVF cells. The ATP assay RLUs were in average 400-500 (data not shown).

C. Example 3. In Vitro Tissue Immunogenicity Testing

A LPS challenge assay was used to assess tissue immunogenicity. Pieces of tissues or cells isolated from collagenase digested tissue (SVF and adipocytes) were incubated in 24-well plates in the presence of 10 µg/mL LPS for tissues and 1 µg/mL LPS for isolated cells for 48 h. Wells without LPS served as a control. After 48 h tissue culture supernatants were collected and tested for the presence of TNF-α using a high-sensitive human TNF Luminex kit (Thermofisher) according to the manufacturer's protocol.

As a part of the assay development fresh adipose tissue prior to and after processing, adipocytes and SVF cells isolated from fresh adipose after the processing, cryopreserved processed adipose and adipocytes and SVF cells isolated from cryopreserved adipose were tested. Devitalized tissue served as a negative control. Results presented in FIG. 4 show that the fresh processed adipose tissue or isolated SVF cells release the highest levels of TNF-α upon LPS stimulation, and that cryopreservation significantly reduces levels of TNF-α. SVF cells isolated from each donor were tested in the LPS challenge assay. For all donors TNF-α levels released from SVF cells after stimulation with LPS were approximately 50 or less pg/mL, which corresponds to 5 mL of the processed viable cryopreserved human adipose tissue product.

D. Example 4. Structure of Viable Cryopreserved and Non-Viable Lyophilized Adipose Tissue Products Thawing and rehydration of cryopreserved and lyophilized adipose tissue: Syringes or vials with cryopreserved adipose were placed in a 37° C. water bath for 3-15 min depending on the volume of the tissue. Vials with lyophilized adipose were reconstituted by adding to the vial 1:1 (V/V) PBS solution.

Microscopic and microscopic appearance: The appearance of adipose tissue was evaluated visually post-thaw or rehydration of the processed adipose tissue, and by placing a small portion of the tissue in the PBS or saline drop in a Petri dish. Microscopic appearance of tissue was performed by light microscopy and by fluorescent microscopy after tissue staining with Calcein.

Figure 5:
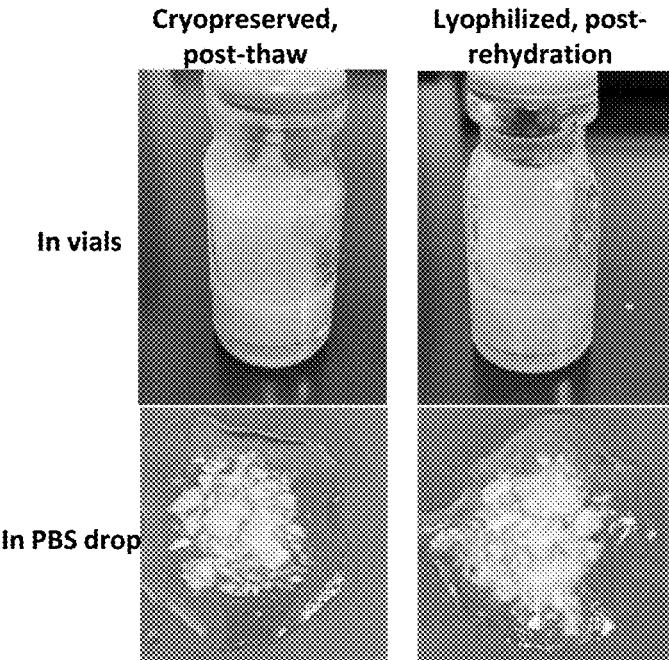
FIG. 5 shows visual appearance of human cryopreserved and lyophilized processed adipose tissue products.
Figures 6A, 6B:
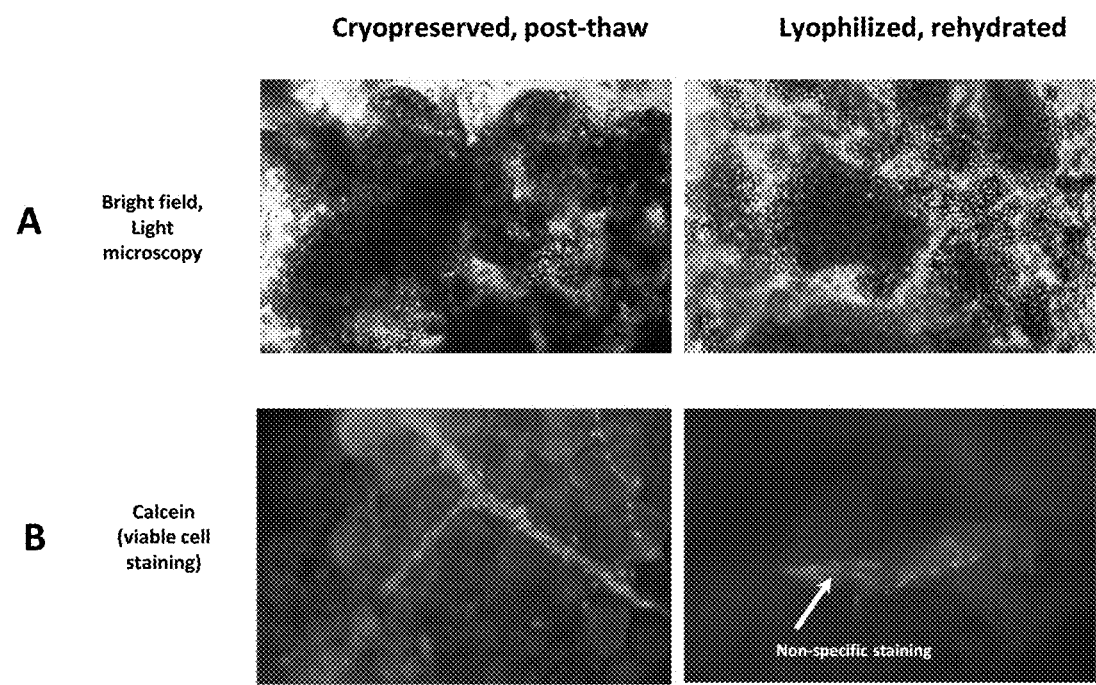
FIGS. 6A and 6B shows microscopic appearance of viable cryopreserved and non-viable lyophilized human adipose tissue products in the bright field light microscopy (FIG. 6A) and Calcein stained samples in the fluorescent microscopy (FIG. 6B).

Post-thaw and after rehydration human adipose tissue products have similar macroscopic (FIG. 5) and microscopic appearance in a bright light field (FIG. 6A). Fluorescent microscopy of Calcein-stained tissues shows the presence of viable adipocytes and structured blood vessels with viable cells in the cryopreserved tissue (FIG. 6B, left image). However, there are no blood vessels and viable cells in lyophilized tissue (FIG. 6B, right image). The white arrow points to non-specific stained structure that may represent remaining matrix of the blood vessel.

Injectability: The injectability of the processed cryopreserved and lyophilized adipose was tested by passing the tissue through needles of different sizes. Both, types of product were going through 20G needles.

Histological evaluation: Fresh human adipose tissues prior to and after processing, cryopreserved post-thaw and lyophilized after rehydration were fixed in formalin for histological analysis. Fixed samples were stained by hematoxylin and eosin (H&E) according to the standard protocol at a certified histology lab. Stained samples were evaluated by an independent certified pathologist. Images of H&E stained adipose are shown in FIG. 7. The structure of all samples is consistent with the structure of adipose tissue. There are no significant differences between samples.

E. Example 5. Rehydration Time and Handling Properties of Lyophilized Adipose Rehydration time and handling properties: Glass vials with 2 mL lyophilized human adipose in different preservation solutions were reconstituted in 2 mL saline within 7 days and 3.5 months after lyophilization. A vial with adipose tissue cryopreserved in DMSO was used as a control. Time required for complete rehydration of the lyophilized tissue was recorded. After complete rehydration the handling properties of each sample were evaluated: stickiness, ease of transfer from a vial into a syringe, and injectability. Visual and microscopic appearance of each sample were also evaluated.

Table 5 summarizes all observations. Results show that without a preservative the tissue is difficult to rehydrate, and to transfer from the vial into a syringe. Rehydration of adipose lyophilized without preservatives took >15 min with vortexing. Tissue was "clumped" in one big aggregate. Lyophilized adipose samples in the presence of DMSO or trehalose rehydrated instantly when rehydration was performed within 7 days after lyophilization. However, 3.5 months later rehydration of lyophilized adipose containing DMSO took 5-7 min. The trehalose containing sample rehydrated instantly. Pieces of tissue in DMSO-containing sample were sticky with free lipids released from dead adipocytes. The trehalose-containing sample was not sticky and visually had no free lipids. These data indicate that trehalose is a better preservative for human adipose tissue lyophilization.

Table 5 shows rehydration time and handling properties of lyophilized adipose

| Sample | Rehydration time | Handling properties | Visual & microscopic appearance of rehydrated adipose |
|---|---|---|---|
| Rehydration within 7 days post lyophilization | | | |
| No preservative | >15 min, vortex required | Tissue particles are sticky, difficult to transfer the tissue from the vial into a syringe | Same as the cryopreserved tissue post-thaw |
| Trehalose | Instant | Tissue particles are not sticky, easy to transfer the tissue from the vial into a syringe | Same as the cryopreserved tissue post-thaw |
| DMSO | Instant | Tissue particles are stickier than the sample without preservatives, but it is easy to transfer the tissue from the vial into syringe | Same as the cryopreserved tissue post-thaw |
| DMSO (cryopreserved control) | Not applicable | Tissue particles are not sticky, easy to transfer the tissue from the vial into a syringe | Not applicable, this sample was used as a reference control |
| Rehydration 3.5 months of storage at room temperature post lyophilization | | | |
| DMSO | 5-7 min | Tissue particles were sticky, more difficult to transfer from the vial into a syringe | Free lipids were present in large amount |
| Trehalose | Instant | Tissue particles are not sticky, easy to transfer the tissue from the vial into a syringe | Same as the tissue was within 7 days post-lyophilization |

F. Example 6. Human Adipose Testing In Vivo in Mouse Models

These studies were conducted in compliance with the current version of the following: 1) Animal Welfare Act Regulations (9 CFR); 2) U.S. Public Health Service Office of Laboratory Animal Welfare (OLAW) Policy on Humane Care and Use of Laboratory Animals; 3) Guide for the Care and Use of Laboratory Animals (Institute of Laboratory Animal Resources, Commission on Life Sciences, National Research Council, 1996); and 4) AAALACi accreditation. Procedures used in this study have been designed to avoid or minimize unacceptable discomfort, distress or pain to the animals.

Figure 8:
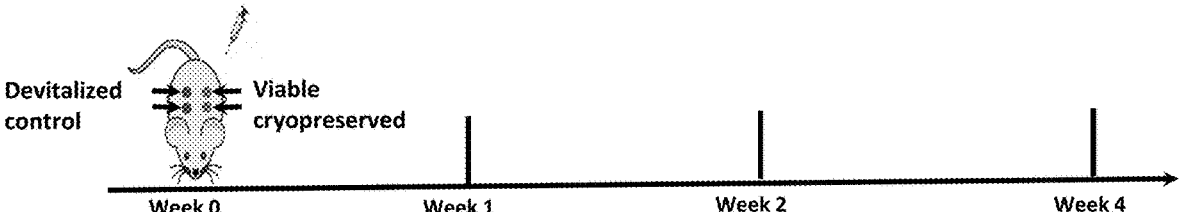
FIG. 8 shows "Evaluation of an inflammatory response against cryopreserved devitalized and viable human adipose tissue in an immune competent mouse model" study design. Ten 8 weeks old female FVB.129P2-Pde60/AntJ mice received subcutaneous injections of ~0.25-0.3 mL/point of devitalized and viable cryopreserved human adipose tissue grafts. Gross examination & sample collection (n=3, for 4 weeks—n=4): ½ each graft—fixed for histology; ½ each graft—frozen for cytokine & human cell analysis; Mouse adipose—for histology (reference control).

1. Study #1: Evaluation of an Inflammatory Response Against Cryopreserved Devitalized and Viable Human Adipose Tissue in an Immune Competent Mouse Model Study design: This study was conducted using ten (10), eight to ten weeks (8-10) weeks old female FVB.129P2-Pde60/AntJ mice. The duration of the study was 4 weeks. After undergoing general anesthesia, 10 mice received subcutaneous injections of ~0.25-0.3 mL/point of devitalized and viable cryopreserved human adipose grafts. The adipose grafts were injected via a 18G needle paravertebrally at 2 points on the left side for devitalized cryopreserved graft, and at 2 points on the right side for viable cryopreserved graft. Each mouse received a total of 4 injections of human adipose. Body weights were taken weekly. Mice (n=3) from each experimental group were sacrificed at weeks 1, 2 and 4 post-injection. FIG. 8 shows the study design.

Sample collection: The skin on the back of each mouse was cut, and the adipose grafts were photographed and dissected out. One devitalized cryopreserved graft and one viable cryopreserved graft from each animal was fixed in formalin for histological analysis, and one devitalized cryopreserved graft and one viable cryopreserved graft from each animal was snap frozen on dry ice for cytokine and gene expression analyses. Two pieces of mouse adipose tissue were collected from one animal and fixed and snap frozen to be used as a reference control for histology and cytokines and gene expression, respectively. Fixed samples were sent to a histology lab, and frozen samples were stored at −80° C. prior to testing.

Histological evaluation: Fixed samples were stained by hematoxylin and eosin (H&E) using a standard protocol at a certified histology lab. Histological analysis included evaluation of tissue inflammation and morphology of H&E stained devitalized and viable cryopreserved human adipose grafts collected from the same animal. Five different fields per each graft type per each animal and time point were evaluated and graded. The parameters included: the presence of cysts, vacuoles and necrotic nodules; inflammation, as evidenced by cell infiltration of the grafts; and the presence of fibrosis and other components of the connective tissue (i.e., collagen and elastic fibrils). Each of these parameters was graded on a semiquantitative scale ranging from 0 to 4 by evaluation of the relative presence of each of the histologic parameters in the slide under examination, as follows: 0 (absence), 1 (minimal presence, —25%), 3 (moderate presence, —50%), 4 (extensive presence 75%). Mean semiquantitative scores for 5 fields of the lyophilized grafts were compared to the score for the cryopreserved grafts at each time point. The presence of fibrosis and other components of the connective tissue (i.e., collagen and elastic fibrils) was confirmed by Masson's trichrome staining of devitalized and viable cryopreserved human adipose grafts at week 4. Immunohistochemical staining of devitalized and viable cryopreserved human adipose grafts at weeks 4 with mouse F4/80, mouse CD3 and human KU80 was performed to detect infiltration of grafts with mouse macrophages and T-cells, and to detect the presence of human cells in grafts, respectively. Histological staining was performed at a certified histology lab, and all samples were evaluated by a certified independent pathologist.

Figure 9:
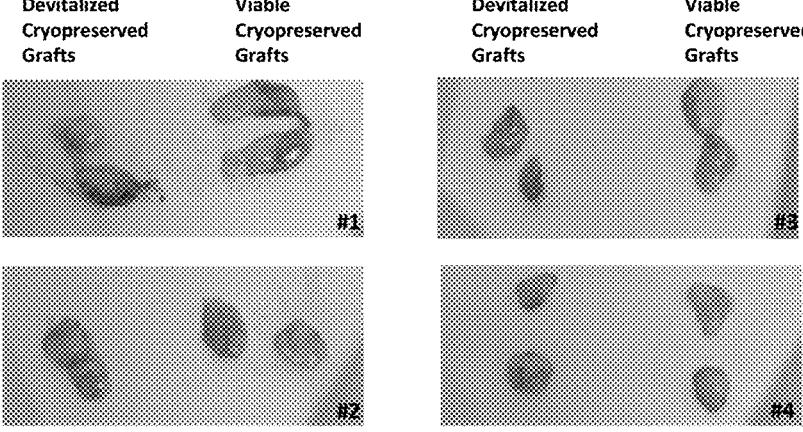
FIG. 9 shows visual appearance of dissected cryopreserved devitalized and viable human adipose tissue grafts from 4 animals (#1-4) 4 weeks post-implantation.

FIG. 9 shows visual appearance of devitalized (the left side on each photograph) versus viable (the right side on each photograph) cryopreserved human adipose grafts excised from fully immunocompetent mice 4 weeks after implantation. All grafts were present in mice after 4 weeks without significant differences between grafts.

Figure 10:
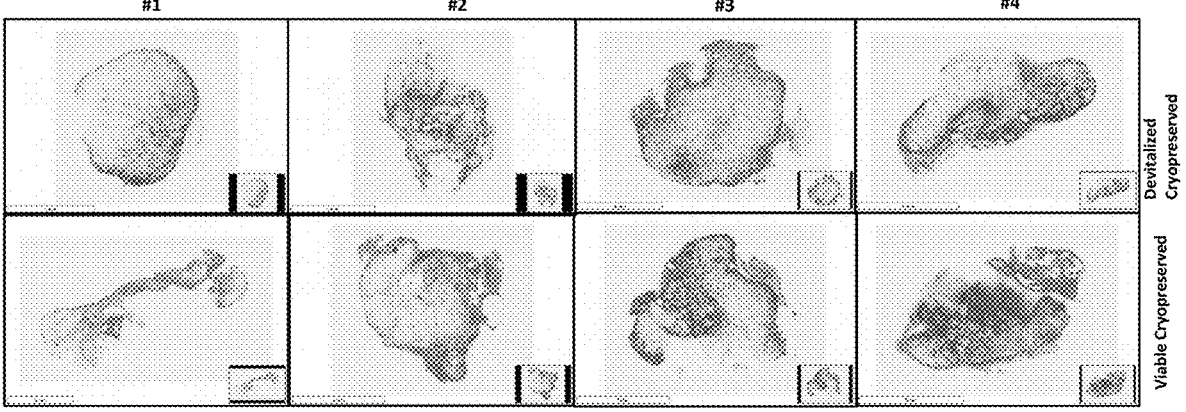
FIG. 10 shows H&E histological staining of dissected cryopreserved devitalized and viable human adipose tissue grafts from 4 animals (#1-4) 4 weeks post-implantation.

The structure of the excised grafts after 4 weeks post-implantation was evaluated histologically using H&E-stained sections. FIG. 10 shows H&E-stained graft section at low magnification. H&E staining shows that there are no significant differences between devitalized vs viable cryopreserved grafts. The lack of significant differences was confirmed by histological scores (Table 6). It was an unexpected finding, particularly for inflammation scores: although the inflammation score was higher (=more inflammatory response against human antigens) for the viable cryopreserved grafts the difference was not statistically significant (Table 6). Another unexpected finding is that the mechanism of tissue remodeling is similar for both devitalized (no living human cell in the graft) and viable human cryopreserved adipose grafts. Masson's trichrome (MT) staining shows the same amount and pattern of collagen deposition in both grafts (FIG. 11, two images on the left), and in both grafts there are areas representing human adipose tissue necrosis and regenerated new adipose tissue (FIG. 11, images on the right), which are consistent with the appearance of normal mouse adipose (FIG. 11, the bottom image on the right).

Table 6 shows mean histological scores for devitalized versus viable cryopreserved human adipose grafts excised from fully immunocompetent mice 4 weeks after implantation

| | WEEK 4, Histological Scores (Mean ± SD) | | |
|---|---|---|---|
| Evaluation Parameters: | Devitalized Cryopreserved Graft | Viable Cryopreserved Graft | P |
| Integrity | 2.25 ± 0.50 | 2.00 ± 1.15 | 0.761 |
| Oil Vacuoles | 2.00 ± 0.00 | 2.00 ± 1.15 | 1.00 |
| Fibrosis | 2.75 ± 0.50 | 2.00 ± 0.82 | 0.058 |
| Inflammation | 1.00 ± 0.00 | 1.5 ± 0.58 | 0.182 |

Figure 12:
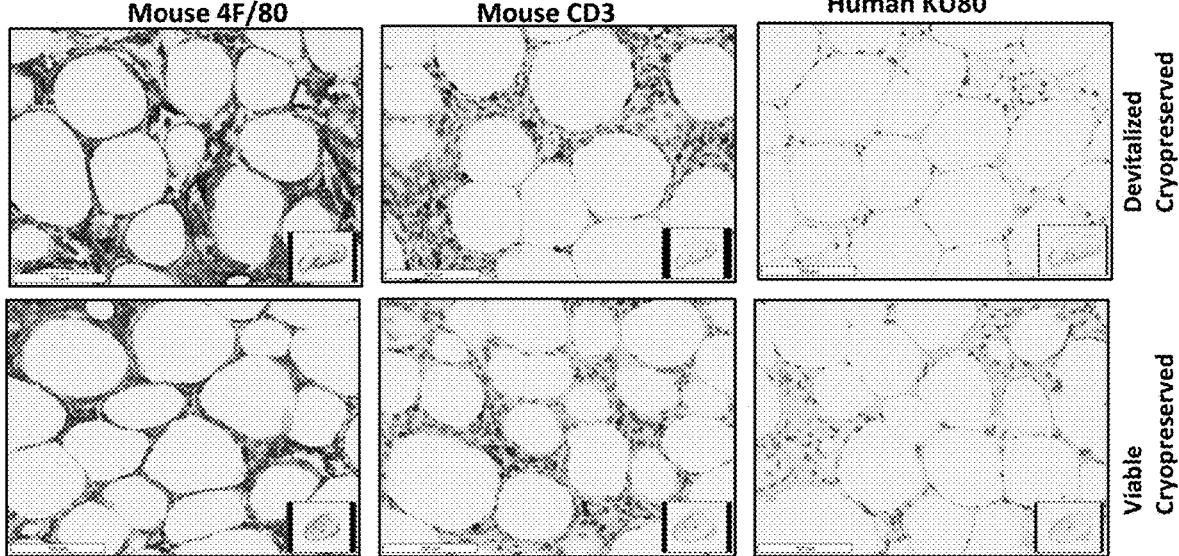
FIG. 12 shows immunohistochemical staining of dissected cryopreserved devitalized and viable human adipose tissue grafts 4 weeks post-implantation at 20× magnification. Mouse 4F/80 marker detects mouse macrophages, mouse CD3 marker detects mouse T-lymphocytes and human KU-80 marker detects the presence of human cells in the adipose grafts.

The grafts excised from mice after 4 weeks post-implantation were further evaluated using immunohistochemical staining. The staining provided answers to two important questions: 1. To identify types of immune cells that infiltrated the grafts; and 2. To detect the human cells in the grafts. FIG. 12 summarizes the results. In both grafts the major type of mouse immune cells infiltrating the grafts are macrophages (FIG. 12, left images stained for 4F/80 mouse macrophages marker). Mouse T-cells also infiltrated the grafts (FIG. 12, middle images); however, the amount of T-cells is significantly lower as compared to the amount of macrophages. There were no differences between human adipose grafts in the level of infiltration by macrophages and T-cells. This result indicates that the inflammatory and immune responses to the graft material is mediated by human antigens rather than by the presence of living human cells in the viable cryopreserved human adipose graft.

Staining of human adipose grafts with human nuclear KU80 antigen shows that there are no human cells detectable in both grafts 4 weeks after the implantation (FIG. 12, images on the right).

In summary, key findings of the study were: a) both grafts after 4 weeks post-implantation had similar appearance and size; b) human cells were not detectable in both grafts 4 weeks post-implantation; c) the tissue remodeling mechanisms in both grafts include a slow resorption of human adipose and formation of new mouse adipose tissue; d) there were no differences in histological scores for tissue integrity (presence of normal adipose), human adipocyte necrosis, fibrogenesis and inflammation; and e) there were no differences between grafts in the amount of infiltrating macrophages and T-cells.

Figure 13:
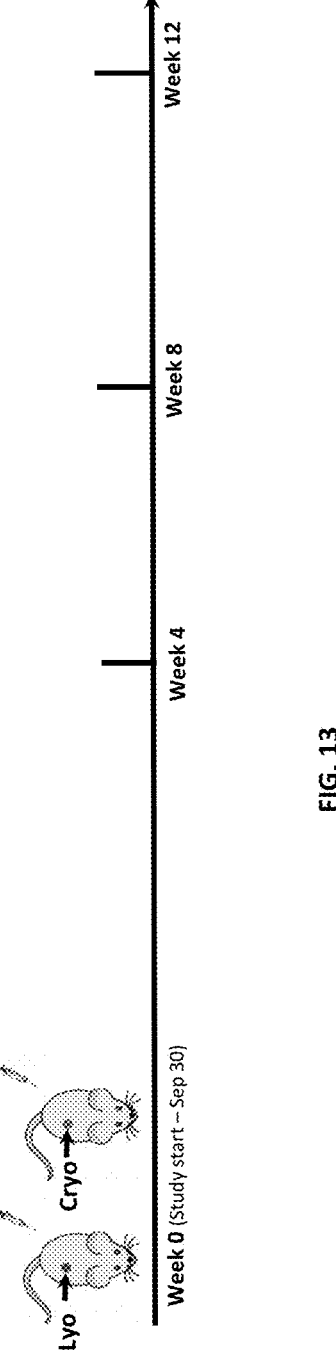
FIG. 13 shows "Evaluation of lyophilized and cryopreserved human adipose graft's remodeling in nude mice" study design. 18 female Nude mice were randomly divided into 2 groups. All mice received subcutaneous injections of 0.5 mL of human adipose tissue grafts A (group 1, n=9) and B (group 2, n=9) on the dorsum. All animals received pain medications for 3 days post injection to reduce inflammation. Baseline and week 1 blood serum was collected from 6 animals (n=3, Graft A and n=3, Graft B) assigned to "week 4" groups. Gross examination & sample collection (n=3/ group, n=6 total): Each graft was weighed; ½ Graft A and B—fixed for histology; ½ Graft A and B—cytokines/human cells.

2. Study #2: Evaluation of Lyophilized and Cryopreserved Human Adipose Graft's Remodeling in Nude Mice i. Study Design:

The study was conducted using eighteen (18), six to eight weeks (6-8) weeks old female athymic nude mice. The duration of the study was 12 weeks. Mice were randomly assigned to two groups (n=9) with n=3 within each group for study time point 4, 8 and 12 weeks. After undergoing general anesthesia, 18 mice received subcutaneous injections of 0.5 mL of lyophilized or cryopreserved human adipose (n=9 per group). The adipose grafts were injected subcutaneously on the back of each mouse via a 20G needle. Pain was controlled by pain medication, Buprenorphine is 0.05-0.1 mg/kg SQ, q8-12 hr for 2-3 days post injection. Inflammation was controlled by Rimadyl (Carprofen): dose is 5 mg/kg SQ, q24 hr. On the day of the injection a baseline blood serum sample were collected from 3 mice from each group assigned to the time point "4 weeks" (total n=6) prior to graft's injection. Remaining graft materials post-injection was fixed and sent for histological evaluation. At week 1 post-injection blood serum samples were collected from the same 6 mice (n=3 per group) assigned to the time point "4 weeks". Body weights were measured weekly. FIG. 13 shows the study design.

Adipose graft collection at weeks 4, 8 and 12: Mice (n=3) from each experimental group were sacrificed at weeks 4, 8 and 12 post-injection. The skin on the back of each mouse was cut, and the adipose grafts were photographed and dissected out. Each graft was weighed, and then divided into 2 halves. One half of the graft from each animal was fixed in formalin for histological analysis, and another half of the graft from each animal was collected in a tube with medium for cytokine and cellular analyses. Fixed samples were sent to a histology lab together with the samples of fixed adipose grafts prior to injection. Samples collected in the medium were used for cell analysis.

Figure 14A:
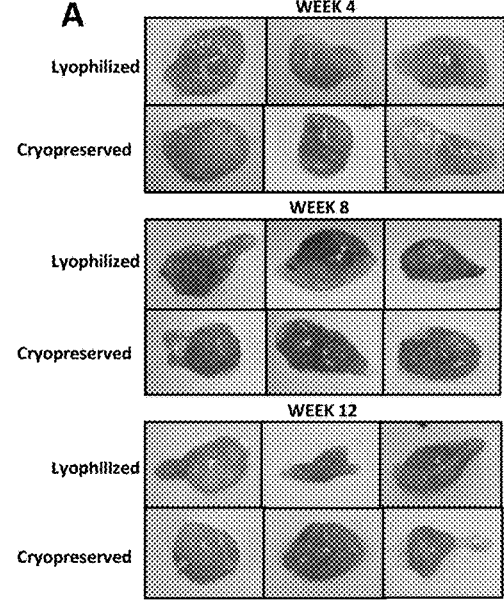
FIGS. 14A and 14B show visual appearance (FIG. 14A) and weight (FIG. 14B) of lyophilized and cryopreserved human adipose grafts at week 4, 8 and 12 post-implantation.
Figure 14B:
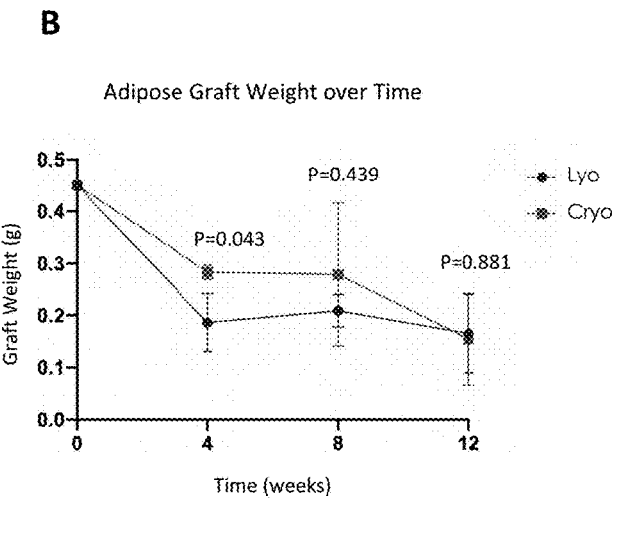

FIG. 14 shows visual appearance (FIG. 14A) and weights (FIG. 14B) of lyophilized and cryopreserved human adipose grafts excised from nude mice at week 4, 8 and 12 post-implantation. Images on the left show that there are no significant differences between grafts. The graph on the right (FIG. 14B) shows that the main drop in weight for both grafts happened by week 4. At week 4 the cryopreserved human adipose grafts were larger than the lyophilized grafts. However, at the later time points of the study (weeks 8 and 12) the weights of the cryopreserved and lyophilized grafts are similar. By week 12 both grafts retained 40% of the initial weight. These data are consistent with data in the literature for fresh human adipose grafts in nude animals.

Histological evaluation: Fixed samples were stained by hematoxylin and eosin (H&E). Histological analysis included evaluation of tissue integrity and remodeling over time of H&E-stained lyophilized and cryopreserved human adipose grafts. Five different fields per each graft type per each animal and time point were evaluated and graded. The parameters include: the presence of cysts, vacuoles and necrotic nodules; inflammation, as evidenced by cell infiltration of the grafts; and the presence of fibrosis and other components of the connective tissue (i.e., collagen and elastic fibrils). Each of these parameters was graded on a semiquantitative scale ranging from 0 to 4 by evaluation of the relative presence of each of the histologic parameters in the slide under examination, as follows: 0 (absence), 1

The cryopreserved graft has a small necrotic area, and the large part of the graft is filled with normal adipose tissue. The summary of histological scores for the lyophilized and cryopreserved grafts is presented in Table 7. The key difference between the lyophilized and the cryopreserved grafts is as expected in tissue integrity. The cryopreserved graft structure has areas of dead and normal adipose tissue. The cells in the lyophilized graft were devitalized, which is clearly seen on the tissue sections (FIG. 15); however, over time the number and the volume of large lipid vacuoles released from dead adipocytes is decreasing, which indicates ongoing remodeling of the graft (Table 7, scores for "oil vacuoles"). Another interesting finding is that the scores for inflammation is trending lower for the lyophilized grafts than the inflammation scores for the cryopreserved grafts (Table 7).

Thus, histological analysis shows that the lyophilized graft is remodeling into a connective tissue. The finding that the lyophilized graft will be not resorbed, but remodeled is a new finding.

Table 7 shows mean histological scores for devitalized lyophilized versus viable cryopreserved human adipose grafts excised from nude mice at 4, 8 or 12 weeks after implantation

| | Histological Scores (Mean ± SD) | | | | | | | | |
|---|---|---|---|---|---|---|---|---|---|
| | WEEK 4 | | | WEEK 8 | | | WEEK 12 | | |
| Evaluation Parameters: | Lyophilized Graft | Cryopreserved Graft | P | Lyophilized Graft | Cryopreserved Graft | P | Lyophilized Graft | Cryopreserved Graft | P |
| Integrity | 1.00 ± 1.00 | 3.67 ± 0.58 | 0.016 | 1.00 ± 0.00 | 3.00 ± 1.00 | 0.026 | 1.00 ± 0.00 | 3.00 ± 1.00 | 0.026 |
| Oil Vacuoles | 3.33 ± 1.15 | 0.67 ± 0.58 | 0.023 | 3.00 ± 0.00 | 2.00 ± 1.00 | 0.16 | 2.67 ± 1.53 | 1.33 ± 0.58 | 0.23 |
| Fibrosis | 2.33 ± 0.58 | 0.67 ± 1.15 | 0.089 | 2.33 ± 0.58 | 1.67 ± 0.58 | 0.23 | 2.33 ± 0.58 | 2.0 ± 0.00 | 0.37 |
| Inflammation | 2.00 ± 0.00 | 1.67 ± 0.58 | 0.37 | 1.67 ± 1.15 | 2.00 ± 0.00 | 0.64 | 1.00 ± 0.00 | 2.67 ± 1.15 | 0.067 |

(minimal presence, ~25%), 3 (moderate presence, ~50%), 4 (extensive presence, 75%). Mean semiquantitative scores for 5 fields of the lyophilized grafts were compared to the score for the cryopreserved grafts at each time point. The structure of H&E-stained lyophilized and cryopreserved adipose graft prior to injection was also evaluated. The presence of fibrosis and other components of the connective tissue (i.e., collagen and elastic fibrils) was confirmed by Masson's trichrome staining of lyophilized and cryopreserved adipose grafts at weeks 4 and 12. Immunohistochemical staining of lyophilized and cryopreserved grafts at weeks 4 and 12 with mouse CD31, mouse Ki-67 and human CD36 was performed to detect new blood vessels, proliferating cells and presence of human adipocytes in grafts, respectively. Histological staining was performed at a certified histology lab, and all samples were evaluated by a certified independent pathologist.

Figure 15:
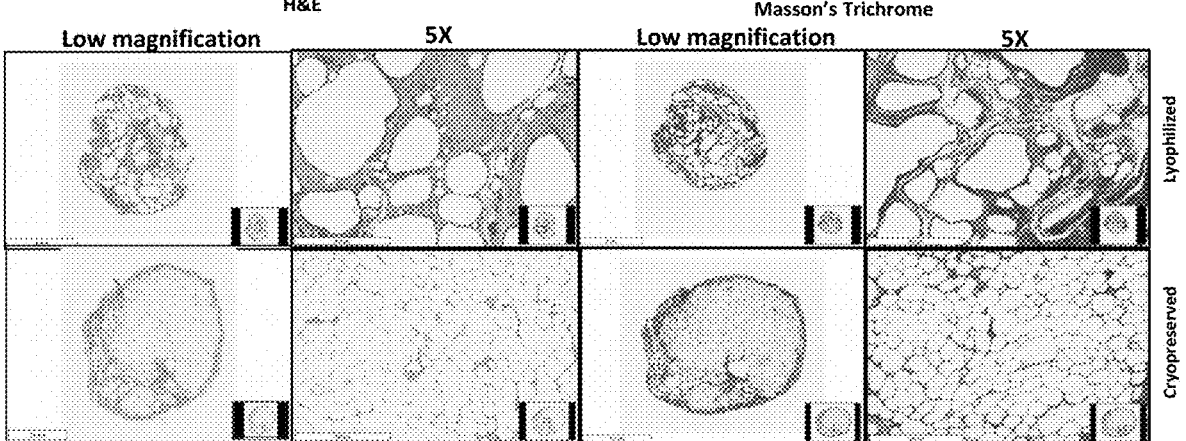
FIG. 15 shows representative images of Hematoxylin & Eosin (H&E) and Masson's Trichrome (MT) histological staining of dissected lyophilized and cryopreserved human adipose grafts 12 weeks post-implantation.

The structure of the excised grafts after 4, 8 and 12 weeks post-implantation was evaluated histologically using H&E and MT-stained sections. FIG. 15 shows representative images of H&E and MT-stained grafts at 12 weeks post-implantation. H&E staining reveals that the lyophilized graft contains large lipid vacuoles released from devitalized adipocytes in the graft, and cryopreserved graft structure largely is consistent with the structure of normal adipose tissue (left images at two magnifications). MT staining reveals that the lyophilized graft has collagen deposition across the entire graft (blue colored areas of the graft), and the cryopreserved graft has collagen deposition only the periphery of the graft (right images at two magnifications).

Figure 16:
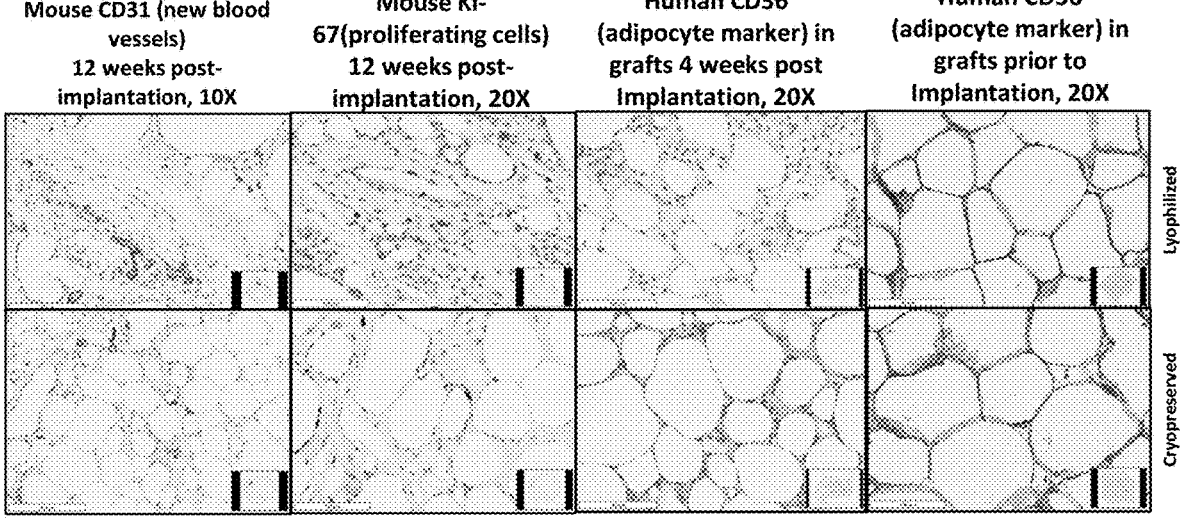
FIG. 16 shows representative images of immunohistochemical staining of dissected lyophilized and cryopreserved human adipose grafts.

The grafts excised from mice after 4 and 12 weeks post-implantation were further evaluated using immunohistochemical staining. The staining provided answers regarding vascularization (staining for mouse CD31 endothelial cell marker) of the grafts and the presence of proliferating cells in the grafts (staining for mouse Ki-67 marker of proliferating cells). Results show that both lyophilized and cryopreserved grafts have newly formed mouse blood vessels in the grafts already by week 4 (data not shown) and blood vessels present at week 12 (FIG. 16, left images). There are no differences in vascularization between the lyophilized and the cryopreserved grafts with pathologist's scores of "+++", corresponding to a high number of blood vessels across the grafts. Staining with mouse Ki-67 revealed that both grafts contain mouse proliferating cells at 4 and at 12 weeks (FIG. 16, second from the left images). There are no differences in number of mouse proliferating cells between the lyophilized and the cryopreserved grafts with pathologist's scores of "+", corresponding to a low number of proliferating cell across the grafts. The presence of proliferating cells in the grafts indicates that the remodeling process is still ongoing in both grafts.

To answer a question regarding the origin of adipose tissue the excised lyophilized and cryopreserved human adipose grafts from animals were stained with the CD36 antibody, a marker for human adipocytes. Staining shows that there are no detectable human adipocytes in both lyophilized (served as a negative control) and cryopreserved grafts already at 4 weeks post-implantation (FIG. 16, 3rd panel of images from the left). This result indicates that the adipose tissue in the cryopreserved grafts is newly formed mouse adipose, which replaces human adipose in the graft. The panel of images on the right in FIG. 16 shows that both lyophilized and cryopreserved grafts prior to implantation were positive for human CD36 adipocyte marker. It indicates that the process developed for the lyophilized adipose tissue product retained integrity of the devitalized adipocytes as it is seen by the positive membrane CD36 staining (FIG. 16, the right bottom image) and by H&E staining of the lyophilized grafts (FIG. 7, 3rd image from the left).

ii. Detection of Human Adiponectin in Serum of Nude Mice Grafted with Lyophilized or Cryopreserved Adipose Grafts:

Mouse serum was collected at baseline (prior to injection of human adipose grafts) and 1 week post-grafting. Serum was tested at 2- and 4-fold dilutions with the assay diluent for the presence of human adiponectin using Luminex according to the standard protocol. Mouse serum prior to human adipose injection served as a negative baseline control. The baseline control mouse serum with spiked human recombinant adiponectin served as a positive control. Results show that human adiponectin was not detectable in mouse serum. This result confirms the lack of systemic effect of the implanted adipose tissue.

iii. Analysis of Adipose Grafts Excised from Nude Mice:

a. Isolation and Culturing of Cells from Lyophilized and Cryopreserved Adipose Grafts:

3 grafts (½ of the excised material from animals) were pooled in two tubes: one—lyophilized, another—cryopreserved. Cells were isolated from 3 pooled lyophilized and 3 pooled cryopreserved adipose grafts by digestion with collagenase type 2. Pooled grafts were cut into small pieces by scissors and then digested 45 min at 37° C. in 15 mL tubes in 5 mL DMEM+0.25 mL 2% collagenase. Digested tissues were filtered via a 300 μM nylon filters and centrifuged. Cells were counted before centrifugation. Cells were plated in 3 mL complete DMEM-10% FBS in 25 cm² flasks. Culture expanded cells were used in further experiments. A portion of culture expanded cells was cryopreserved for long-term storage.

iv. Detection of Mesenchymal Stem Cells in Lyophilized and Cryopreserved Adipose Grafts Using an Adipogenic Differentiation Assay:

Culture expanded cells from lyophilized and cryopreserved grafts were plated in a 24-well plate. When cells formed a monolayer DMEM-10% FBS was replaced by the adipogenic differentiation medium. Cells in DMEM-10% FBS served as a control. Medium was changed every 3-4 days. Cells were cultured for 2-3 weeks with microscopic assessment for the presence of cells with accumulated lipid vacuoles in the cytoplasm. After 2-3 weeks cells were fixed in wells in 4% formaldehyde and stained with Oil Red 0 for visualization of cells differentiated in adipocytes. Photographs were taken.

v. Detection of Human Cells Isolated from Lyophilized and Cryopreserved Adipose Grafts.

Human KU80 Western Blot: Detection of human cells was performed by Western blotting using human KU-80 nuclear marker. Cells isolated from lyophilized grafts should have only mouse cells (negative control). Human NALM-6 cell lysates were used as a positive control.

Human adiponectin ELISA: Culture supernatants from the adipogenic differentiation of cells isolated from lyophilized and cryopreserved grafts were tested for the presence of human adiponectin by ELISA.

Figures 17A, 17B:
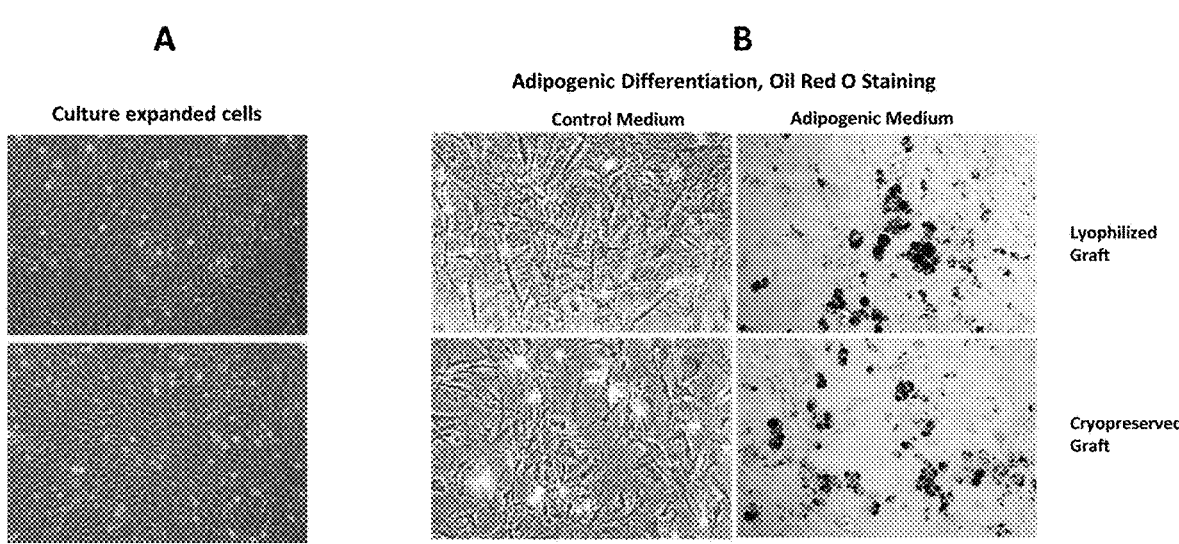
FIGS. 17A and 17B show microscopic images of culture expanded cells from the lyophilized and the cryopreserved grafts (FIG. 17A) and adipogenic differentiation of these cells (FIG. 17B).
Figure 18:
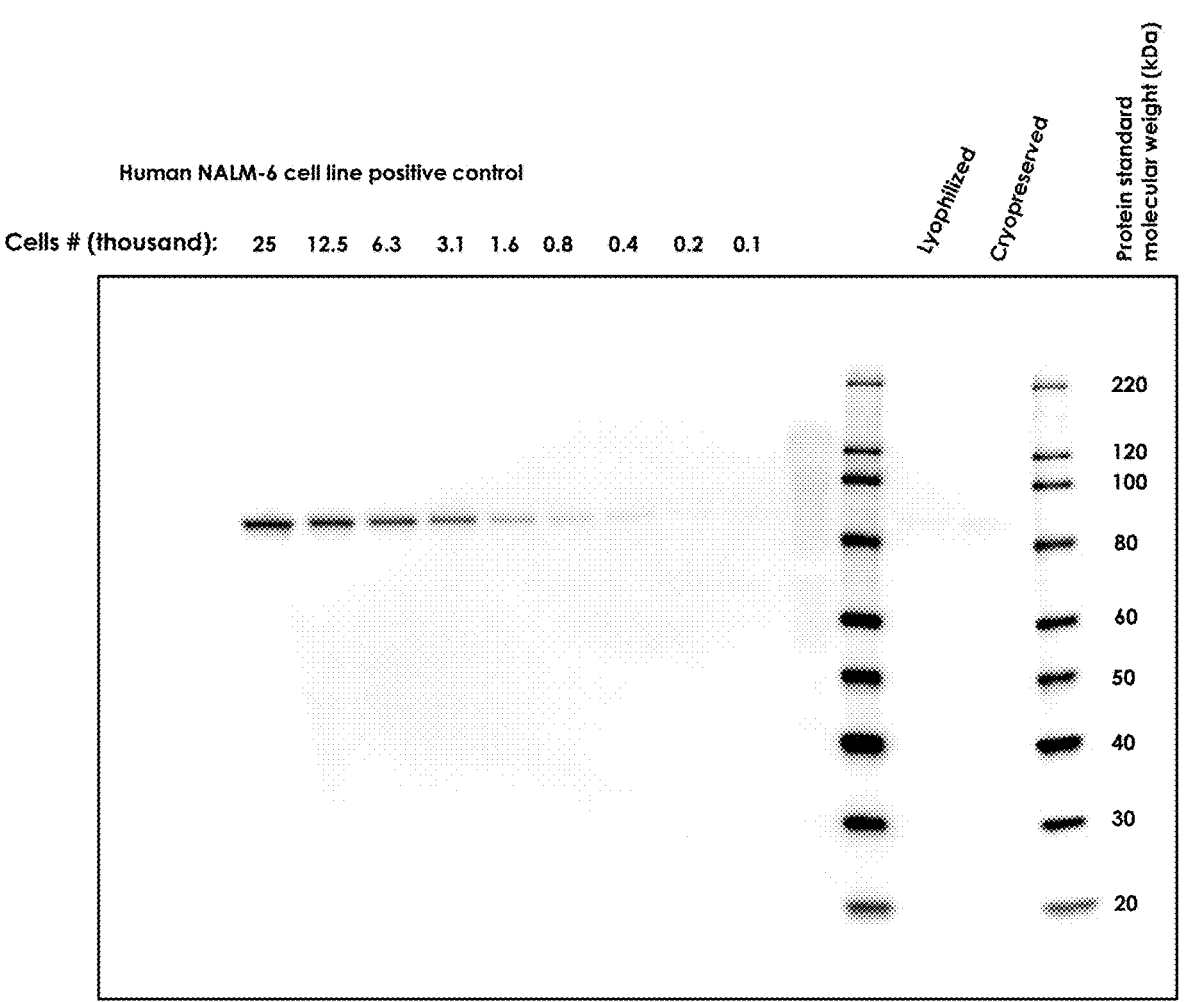
FIG. 18 shows results of human KU80 Western Blot analysis of cells isolated from lyophilized and cryopreserved human adipose grafts. Human NALM-6 cell lysates were used as a positive control.

FIG. 17A shows that both, the lyophilized and the cryopreserved grafts were populated by cells with fibroblast morphology that can be isolated from grafts and grown in the culture flasks. Such cells were isolated from all human adipose grafts at all study time points. Adipogenic differentiation of culture expanded graft's cells demonstrates that some of these cells are mesenchymal stem cells with a potential for differentiation into adipocytes (FIG. 17B). There were no differences in number, viability and adipogenic potential for cells isolated from lyophilized or cryopreserved human adipose grafts excised from nude mice at 4, 8 and 12 weeks study time points. Because lyophilized human adipose grafts had no viable cells all cells isolated from this type of adipose graft are mouse cells. Although immunohistochemical staining of grafts for human CD36 marker did not detect human adipocytes in the cryopreserved human adipose grafts it did not exclude that other types of living human cells could be present in the cryopreserved grafts. The presence of human cells in the grafts was evaluated by Western Blotting (WB) and by testing of culture supernatants from the adipogenesis assay for human adiponectin. WB for human KU80 nuclear antigen did not detect human cells in lyophilized or cryopreserved grafts at 4 weeks study time point (FIG. 18). However, testing of culture supernatants from the adipogenesis assay (FIG. 17B) for human adiponectin by ELISA shows that human mesenchymal stem cells (MSCs) with adipogenic potential are present in the cryopreserved grafts at 4 weeks time point (Table 8). After 4 weeks human MSCs were not detected (Table 8), and thus, at weeks 8 and 12 all cells that were isolated from the cryopreserved grafts and differentiated into adipocytes are mouse cells.

Table 8 shows amount of human adiponectin detected in culture supernatants from the adipogenesis assay using cells from devitalized lyophilized and viable cryopreserved human adipose grafts excised from nude mice at 4, 8 or 12 weeks after implantation

| Graft type: | Time point: | Human adiponectin (pg/mL) | |
| --- | --- | --- | --- |
| | | 4-day SN after 2 weeks of differentiation | 7-day SN after 3 weeks od differentiation |
| Lyophilized | 4 weeks | Below detectable | Below detectable |
| Cryopreserved | 4 weeks | 67 | 566 |
| Lyophilized | 8 weeks | Below detectable | Below detectable |
| Cryopreserved | 8 weeks | Below detectable | Below detectable |
| Lyophilized | 12 weeks | Below detectable | Below detectable |
| Cryopreserved | 12 weeks | Below detectable | Below detectable |

In summary, key findings of the study were: a) there are no differences in visual appearance, weight, vascularization and proliferating cells in the grafts between devitalized lyophilized and viable cryopreserved human adipose tissue products 12 weeks after implantation in mice; b) Viable cryopreserved human adipose tissue product findings: i) Human mesenchymal stem cells persist in the graft in vivo for 4 weeks, and then they disappeared. ii) The graft overtime was replaced by mouse adipose; c) Devitalized lyophilized human adipose tissue product findings: i) Mouse cells including MSCs repopulate the human graft by week 4; ii) The human graft does not trigger inflammation; iii) The human graft is undergoing remodeling into host connective tissue without resorption; iv) Results indicate that devitalized lyophilized human adipose tissue product can be used for soft tissue repair and reconstruction.

G. Example 7. Measurement of Residual Moisture (RM) in Lyophilized Devitalized Adipose Tissues Three vials with lyophilized devitalized adipose tissue representing 3 different lots derived from 3 different donors were tested for residual moisture. Residual moisture was calculated in % based on the initial tissue weight versus tissue weight after treatment in a +105° C. oven for 72 h. Table 9 summarizes the results of testing. The mean RM value for 3 lots was 6.65%.

TABLE 9

| Residual moisture (RM) in lyophilized devitalized adipose tissue | | |
|---|---|---|
| Sample | Sample Description | RM (%) |
| 1 | Lot 001, 2 cc | 6.98 |
| 2 | Lot 002, 2 cc | 4.90 |
| 3 | Lot 003, 2 cc | 8.06 |
| Mean +/− SD | | 6.65 +/− 1.61 |

H. Example 8. In Vitro Evaluation of Non-Radiated and Gamma Radiated Lyophilized Devitalized Adipose Tissue Human adipose was processed as described in example 1. Vials with lyophilized adipose tissue were divided in 3 groups: Group 1—Graft A, non-radiated; Group 2—Graft B, radiated by 15 kGy dose; and Group 3—Graft C, radiated by 30 kGy dose. Grafts A, B, and C were characterized in vitro.

In vitro characterization included: visual appearance, reconstitution time and handling properties ("injectability" test via a 20G needle), tissue structure, free and peroxidized lipids, growth factors and cytokines, and chemotactic activtissues lysates were assessed by measuring Thiobarbituric Acid Reactive Substances (TBARS) using the Parameter™ kit (R&D Systems) according to the manufacturer's instructions. Chemotactic activity of the tissue's extract was tested by migration of human THP-1 cells, a model for macrophage migration, using 24-well transwell plates (Nunc). The number of migrated cells was measured using the ATP assay (the CellTiter-Glo 2.0 assay reagent, Promega). Table 10 below summarizes the test results. Two main differences were identified: tissue color and levels of peroxidized lipids. Non-radiated tissue has a yellow color. After radiation, tissue became white, which might be due to radiation-induced degradation of vitamin A (carotin), known to be deposited in adipose. The most significant finding is that radiation in a dose-dependent manner triggers peroxidation of lipids in the lyophilized devitalized adipose tissue. This might be due to radiation-induced free radical generation leading to lipid peroxidation. It is known that peroxidized lipids are linked to oxidative stress and inflammation. Calculated values of peroxidized lipids in adipose tissue lysates prepared in different lysis buffers are greatly variable. Values of peroxidized lipids for RIPA lysates versus Triton X100 lysates are shown in table 10. However, for all buffers tested results are consistent: peroxidized lipids in non-radiated adipose are lower as compared to the levels of peroxidized lipids in radiated adipose prepared in the same lysis buffer (Table 10).

TABLE 10

| Summary of in vitro characterization of adipose grafts | | | | |
|---|---|---|---|---|
| | Graft Type (Radiation dose in kGy) | | | |
| Graft Characteristics | Graft A (0 kGy) | Graft B (15 kGy) | Graft C (30 kGy) | Comments |
| Appearance | Yellow | White | White | Only color was visually different, See FIG. 1 |
| Reconstitution & handling properties | No significant differences between grafts: all grafts were reconstituted within 30 sec and can be passed via 20 G needles | | | |
| Structure | No significant differences between grafts | | | Assessed histologically using H&E staining |
| Free lipids (in % post reconstitution) | 31.3% | 25.2% | 29.4% | |
| perxxidized lipids (TBARS) | Below quantitation | 1.91 nmol/mg tissue | 3.58 nmol/mg tissue | In RIPA tissue lysates |
| | 3.46 nmol/mg tissue | Not measured, sample was not available | 8.98 nmol/mg tissue | In Triton X100 tissue lysates (optimized method) |
| Growth factors & cytokines | No significant differences between grafts | | | VEGF-A, MCP-1, IL-6, adiponectin |
| Chemotactic activity | All grafts induce migration of human monocyte cell line THP-1; there were no significant differences between grafts | | | The assay was performed in transwell plates | ity. Tissue structure was assessed histologically using H&E staining. Levels of growth factors and cytokines in the tissues were evaluated by ELISA kits (R&D Systems) according to the manufacturer's instructions. Levels of free lipids in the tissues after reconstitution were assessed after centrifugation and expressed in % relative to total volume of adipose and free lipids. Peroxidized lipids in the adipose

I. Example 9. In Vivo Evaluation of Human Adipose Tissue Xenografts in Nude Mice

1. Animal Study Design.

This study was conducted using eighteen (18), six to eight weeks (6-8) weeks old female athymic nude mice. The duration of the study was 8 weeks. Mice were randomly assigned to three groups (n=6 per group) with n=3 within each group for study time point 4 and 8 weeks. After undergoing general anesthesia, 18 mice received subcutaneous injections of 0.5 mL of human adipose graft A, non-radiated tissue, (n=6) or B, 15 kGy radiated tissue (n=6) or C, 30 kGy radiated tissue (n=6). The adipose grafts (2 grafts per animal of the same type) were injected subcutaneously on the left and the right sides on the back of each mouse via a 20G needle. The remaining Grafts A, B, and C post-injections were fixed and sent at the end of the study together with other collected samples for histological evaluation. Pain was controlled by pain medication; Buprenorphine is 0.05-0.1 mg/kg SQ, q8-12 hr for 2-3 days post injection. Inflammation was controlled by Rimadyl (Carprofen); dose is 5 mg/kg SQ, q24 hr. Body weights were measured weekly.

FIG. 19 shows the adipose grafts prior to injection and after injection.

2. Sample Collection at Weeks 4 and 8.

Mice (n=3 per group; n=9 total per time point) from each experimental group were sacrificed at weeks 4 and 8 post-injection. The skin on the back of each mouse was cut, and the adipose grafts were photographed and dissected out. Each graft was weighed and then divided into 2 halves. One half of the graft from each animal was fixed in 10% Neutral Buffer Formalin (NBF) for histological analysis, and another half of the graft from each animal was collected in a tube with medium for cytokine and cellular analyses. Fixed samples were sent to a histology lab. One sample of normal subcutaneous adipose from one mouse at week 4 was also collected and fixed in 10% NBF for histology. This sample was served as a reference control for normal mouse adipose tissue.

3. Histological Evaluation.

Fixed samples were stained by hematoxylin and eosin (H&E). Histological analysis included evaluation of tissue integrity and remodeling over time using H&E-stained human adipose graft A versus graft B and versus graft C. Five different fields per each graft type per each animal and time point were evaluated and graded. The parameters included: the presence of large lipid vacuoles; inflammation, as evidenced by cell infiltration of the grafts; graft vascularization; and the presence of the connective (i.e., collagen and elastic fibrils) and adipose tissue. Each of these parameters was graded on a semiquantitative scale ranging from 0 to 4 by evaluation of the relative presence of each of the histologic parameters in the slide under examination, as follows: 0 (absence, none), 1 (1-25% tissue involved, minimal), 2 (26-50% tissue involved, mild), 3 (51-75% tissue involved, moderate), 4 (76-100% involved, severe). Mean semiquantitative scores for grafts B and C were compared to the mean scores for graft A. The H&E-stained sections of normal mouse adipose and grafts A, B, and C prior to injection served as reference controls. In addition, H&E immunohistochemical staining for CD31 (endothelial cell marker to detect blood vessels) and CD206 (M2 macrophage marker) was performed to demonstrate the presence/absence of blood vessels and M2 macrophages in grafts prior and post-injections.

4. Clinical Observations.

Figure 20:
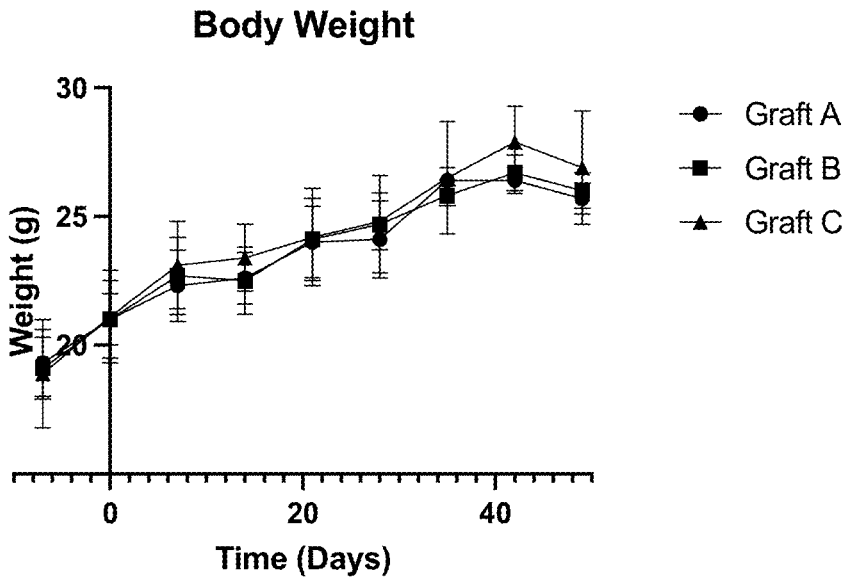
FIG. 20 shows weekly body weights during the study for 3 groups of animals that received Graft A, B, or C. Graphs: mean+/−SD body weight for each time point for 3 groups (n=6 mice for time points days −7 to 28; n=3 for days 35 to 49).

All animals survived until scheduled necropsy. No abnormal behaviors were noted related to the adipose grafts. Body weights were recorded weekly for the duration of study and are presented in Table 11 and FIG. 20. There were no differences in body weight between animals in the 3 groups at all study timepoints.

TABLE 11

| | | | Body Weights<br>Body weights | | | | | | | | |
| | | | Date | | | | | | | | |
| | | | 4-<br>Jan.-<br>2022 | 11-<br>Jan.-<br>2022 | 18-<br>Jan.-<br>2022 | 25-<br>Jan.-<br>2022 | 1-<br>Feb.-<br>2022 | 8-<br>Feb.-<br>2022 | 15-<br>Feb.-<br>2022 | 22-<br>Feb.-<br>2022 | 1-<br>Mar.-<br>2022 |
| Animal | Ear | | Study Day | | | | | | | | |
| Number | Tag | Group | D-7 | D0 | D7 | D14 | D21 | D28 | D35 | D42 | D49 |
| B30-107-001 | 201 | 1 | 17.4 | 19 | 20.4 | 21 | 22.4 | 22.1 | — | — | — |
| B30-107-002 | 202 | 1 | 18.3 | 19.6 | 20.7 | 21.6 | 22.2 | 22.3 | — | — | — |
| B30-107-003 | 203 | 1 | 20.5 | 22.5 | 23.5 | 23.2 | 24.7 | 24.9 | — | — | — |
| B30-107-004 | 204 | 1 | 20 | 22.6 | 23.7 | 23.3 | 25.4 | 25.6 | 26.9 | 26.7 | 25.9 |
| B30-107-005 | 205 | 1 | 18.9 | 21.7 | 23.2 | 23 | 24.6 | 24.6 | 26.3 | 25.8 | 25 |
| B30-107-006 | 206 | 1 | 20.8 | 20.8 | 22.5 | 23.2 | 24.9 | 24.9 | 26 | 26.7 | 26.2 |
| B30-107-007 | 207 | 2 | 20.1 | 21.9 | 23.2 | 23.5 | 25.8 | 26.3 | — | — | — |
| B30-107-008 | 208 | 2 | 17.1 | 19.7 | 21.1 | 20.9 | 22.1 | 23 | — | — | — |
| B30-107-009 | 209 | 2 | 18.3 | 20 | 20.9 | 20.8 | 22.4 | 22 | — | — | — |
| B30-107-010 | 210 | 2 | 19.6 | 22 | 24.5 | 23.6 | 25 | 26.7 | 25.8 | 26.4 | 26.2 |
| B30-107-Oil | 211 | 2 | 20.1 | 21.5 | 23.9 | 23.3 | 25.3 | 26.1 | 26.1 | 27.5 | 26.6 |
| B30-107-012 | 212 | 2 | 19.1 | 20.8 | 22.7 | 22.7 | 23.9 | 24.2 | 25.4 | 26.1 | 25.2 |

TABLE 11-continued

Body Weights
Body weights

| | | | | | | | Date | | | | |
| | | | 4-Jan.-2022 | 11-Jan.-2022 | 18-Jan.-2022 | 25-Jan.-2022 | 1-Feb.-2022 | 8-Feb.-2022 | 15-Feb.-2022 | 22-Feb.-2022 | 1-Mar.-2022 |
| Animal | Ear | | | | | | Study Day | | | | |
| Number | Tag | Group | D-7 | D0 | D7 | D14 | D21 | D28 | D35 | D42 | D49 |
| B30-107-013 | 213 | 3 | 21.6 | 22.1 | 24.3 | 23.3 | 22 | 24.6 | — | — | — |
| B30-107-014 | 214 | 3 | 16.5 | 19.9 | 21.4 | 22.4 | 24.1 | 24.1 | — | — | — |
| B30-107-015 | 215 | 3 | 20.7 | 23.1 | 24.4 | 23.2 | 24.5 | 23.9 | — | — | — |
| B30-107-016 | 216 | 3 | 17.4 | 19.1 | 20.8 | 21.6 | 22.6 | 24.1 | 24 | 26.3 | 24.4 |
| B30-107-017 | 217 | 3 | 19.8 | 23.4 | 24.9 | 25 | 26.6 | 26.8 | 27.7 | 28.5 | 28.5 |
| B30-107-018 | 218 | 3 | 17.4 | 20.6 | 22.8 | 24.7 | 26.5 | 25.4 | 27.8 | 28.9 | 27.7 |

5. Analysis of Grafts: Visual Appearance and Weight

Figure 23:
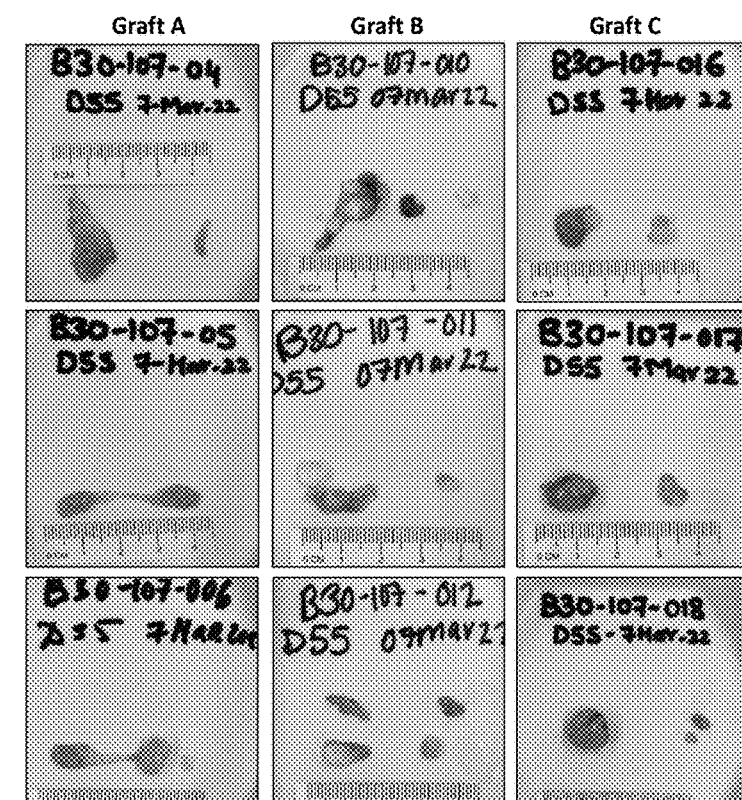
FIG. 23 shows visual appearance of excised adipose grafts A, B, and C at week 8 post-injection (on the right). On the left: the upper image—an example of oil released from graft B from mouse B30-107-010; the middle image—an example of blood vessels in one of grafts C excised from mouse B-30-107-017; lower image shows an aseptic abscess in one of the grafts C excised from mouse B30-107-018.

Mice (n=3 per group for each time point) were sacrificed at weeks 4 and 8 post-injection of adipose grafts. The skin on the back of each mouse was cut, and the adipose grafts were identified and photographed as shown in FIG. 21. Then, the adipose grafts were dissected out, placed in a plastic boat, and photographed (FIGS. 22 and 23). Each graft was weighed. Visual appearance of excised adipose grafts is shown in FIG. 22 for the week 4 time point and in FIG. 23 for the week 8 time point. Two grafts C (mice B30-107-017 and B30-107-018) were large with weights higher than the weight of injected material on day 0. These grafts contained encapsulated cysts inside the grafts that were filled with oil and with pus-like substance for mice B30-107-017 and B30-107-018, respectively.

Figure 24:
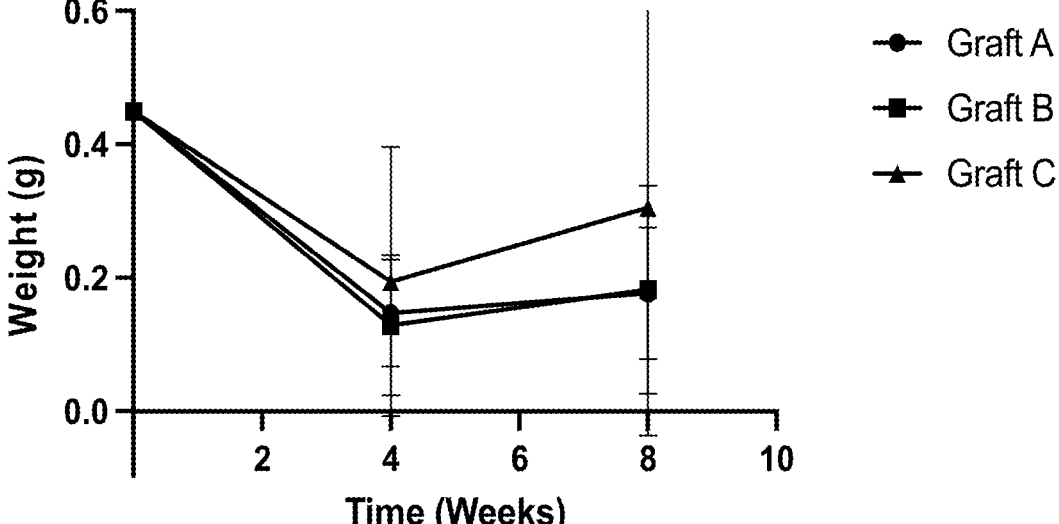
FIG. 24 shows adipose graft weights at weeks 4 and 8 post-injection. Graphs: mean+/−SD graft weight. There was no statistically significant difference between the weights of grafts A, B, and C.

FIG. 24 and FIG. 25 summarize the statistics of the graft weights at weeks 4 and 8. Results demonstrates that the drop in weight happened by week 4 for all three types of grafts without significant changes at week 8. There were no statistically significant differences in weights between grafts A, B and C at both timepoints: 4 and 8 weeks. However, 6 out of 12 grafts B (50%), 5 out of 11 grafts C (45%), and only 1 out of 11 (9%) grafts A (red colored in the table 9.2.1.1; visual appearance of grafts in FIGS. 5 and 6) were resorbed by >80%. Size of grafts A was less variable between grafts with 30-40% tissue retention rate over 8 weeks without a decrease from week 4 to week 8. A significant weight increase for two grafts C in mice B30-107-017 and B30-107-018 was noted. Weight increases were due to encapsulated cysts in the grafts, not due to new tissue formation.

6. Analysis of Grafts: Histology and Immunohistochemistry (IHC)

Figure 26:
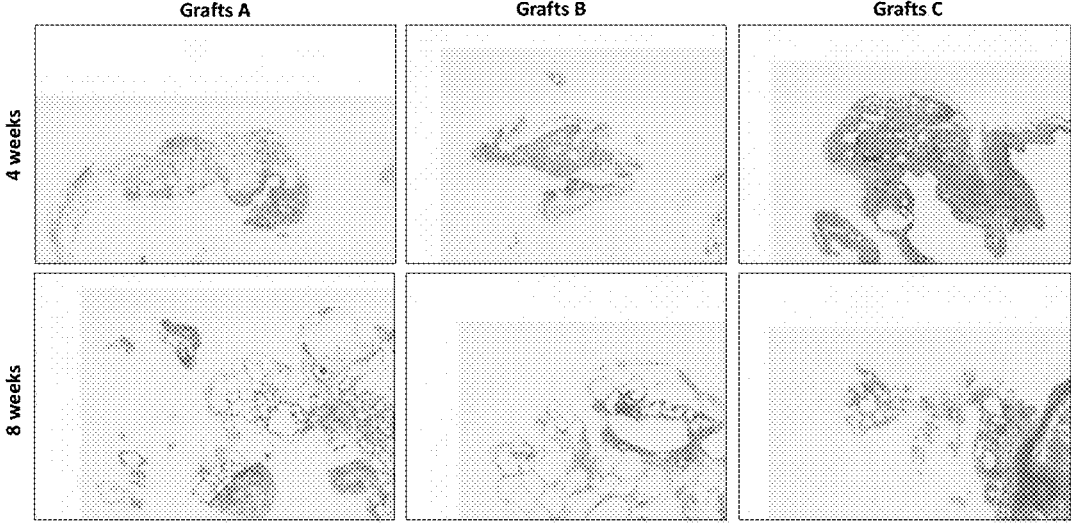
FIG. 26 shows H&E-stained grafts A, B, and C excised at weeks 4 and 8 post-injection at the lowest magnification. Grafts C show a high number of inflammatory cells (purple color) infiltrating the grafts and the formation of encapsulated cysts.
Figure 27:
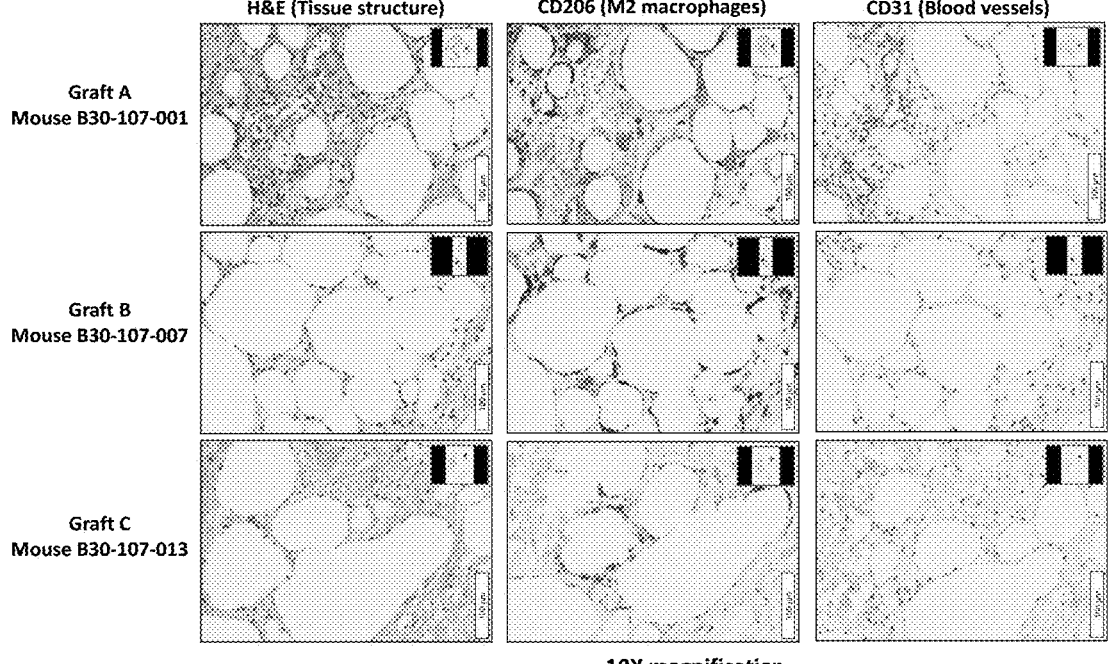
FIG. 27 shows H&E-stained and CD206 and CD31 immunohistochemically stained grafts A, B, and C excised at weeks 4 post-injection at the 10× magnification. Brown color on CD206 and CD31 images represents positively stained cells in the grafts.
Figure 29:
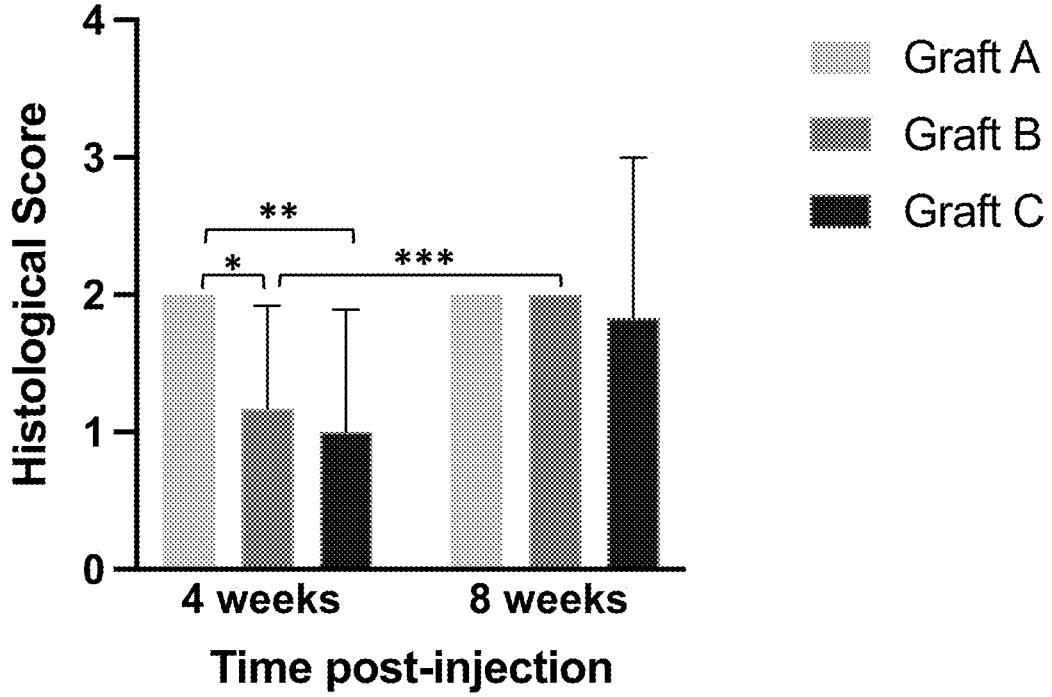
FIG. 29 shows results of the analysis for blood vessels present in the grafts excised from mice at weeks 4 and 8 post-injection. The bar graph shows mean+/−SD histological scores for CD31 (endothelial cell marker). There were statistically significantly more blood vessels in grafts A at week 4 vs grafts B (*P=0.037) and grafts C (P=0.035). At week 8, more blood vessels were developed in grafts B vs in this type of graft at week 4 (*P=0.022).
Figure 31:
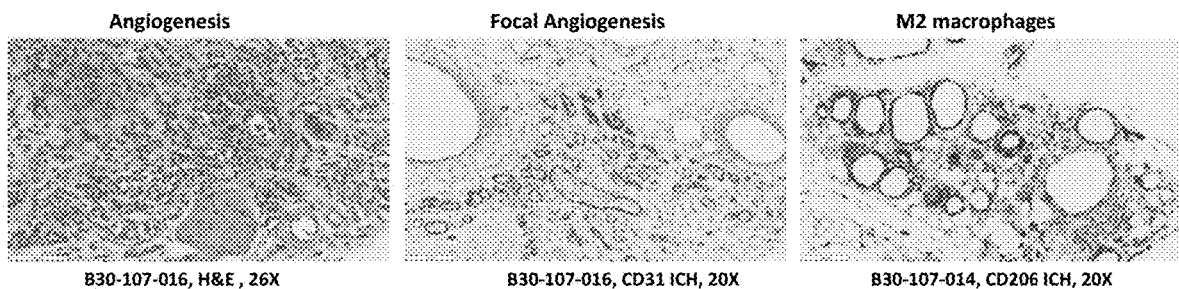
FIG. 31 shows images selected by the study pathologist to demonstrate angiogenesis and the presence of M2 macrophages in adipose grafts post-injection.
Figure 33:
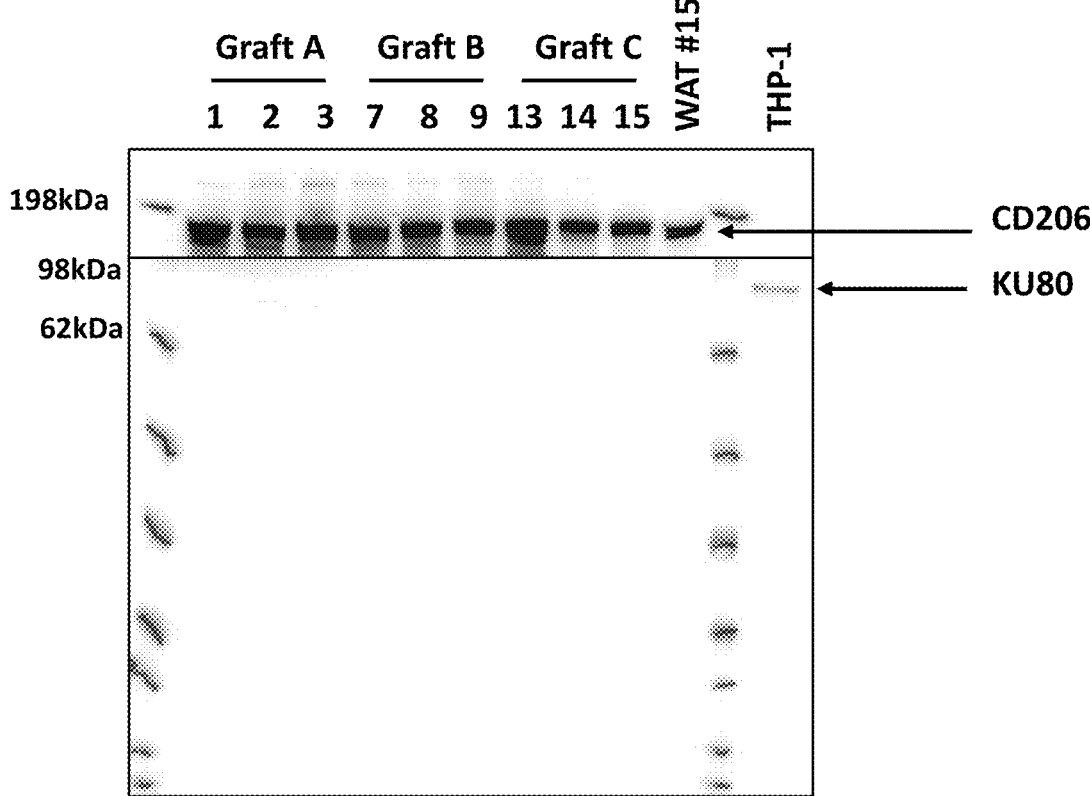
FIG. 33 shows western blot analysis of adipose graft's lysates at 4 weeks after implantation. Results indicate that mouse M2 macrophages (CD206 marker) were present in all grafts. Results also show that there were no detectable human cells in the grafts (KU80 marker). Numbers 1, 2, 3, 7, 8, 9, 13, 14, and 15 are labels for individual animals in the experiment. WAT #15, a normal mouse white adipose tissue, was used as a positive control for M2 macrophages. THP-1, a human monocyte cell line, was used as a positive control for KU80 antigen, which is a marker for human cells.

FIG. 26 shows selected images of H&E-stained grafts A, B, and C excised at weeks 4 and 8 post-injection at small magnification. FIG. 27 shows selected images of H&E histological staining and CD31 and CD206 immunohistochemical (IHC) staining of grafts A, B, and C excised at week 4 post-injection. Histological analysis and scoring of stained adipose graft sections was performed by an independent pathologist. Summary of histological scores (mean+/SD) for 2 time points combined are presented in FIG. 28. Scores between grafts A, B, and C were not statistically significant with the exception of blood vessel formation. Analyses demonstrated statistically significant increased blood vessel formation in grafts A vs grafts B and C at week 4 (FIG. 29). Analyses also demonstrated that Grafts A had better tissue integrity defined by a combination of: i) higher scores for fat small droplets representing adipose and new blood vessel formation; ii) by lower scores for fat large droplets, for large clear spaces representing cysts without capsules and for inflammation; and iii) by absence of large sized cysts and encapsulated cysts (FIG. 28). Five out of 10 grafts C contained large sized cysts, two of which were encapsulated cysts with a higher degree of graft infiltration by inflammatory cells. Graft C from mouse B30-107-018 had a large sterile encapsulated abscess (FIG. 30). Adipose grafts post-injection were infiltrated with mouse M2 macrophages, which is described in the literature as beneficial for remodeling of adipose grafts (FIG. 31).

In summary, results demonstrate that all grafts lost weight during the first 4 weeks without significant changes between week 4 and week 8. There were no statistically significant differences in weights between grafts A, B, and C. However, ~50% of grafts B and C versus 9% of grafts A were resorbed by >80%. Histologically, after injection all grafts were infiltrated by M2 macrophages and contained newly formed blood vessels. Formation of fibrous connective tissue in the grafts was noted. Histologically, Grafts A had better tissue integrity defined as a combination of histological scores. The main difference between grafts was the absence of encapsulated cysts in grafts A and B. Grafts C contained large encapsulated cysts with a higher degree of graft infiltration with inflammatory cells, and one graft C contained an encapsulated sterile abscess.

j. Example 11. In Vitro Analysis of Adipose Grafts Excised from Nude Mice 8 Weeks Post-Injection Mice (n=3 per group; n=9 total per time point) from each experimental group were sacrificed at weeks 4 and 8 post-injection. The skin on the back of each mouse was cut, and the adipose grafts were photographed and dissected out (FIGS. 21, 22, and 23). Each graft was weighed and then divided into 2 halves. One half of the graft from each animal was fixed in 10% Neutral Buffer Formalin (NBF) for histological analysis (results are described in the section "Analysis of grafts: histology and immunohistochemistry"), and another half of the graft from each animal was collected in a tube with medium for detection of mouse TNF-α, peroxidized lipids, M2 macrophages, and human cells in the grafts.

Levels of mouse TNF-α in the adipose grafts collected 8 weeks after injection were measured using high sensitivity mouse TNF-α Luminex kit (Thermofisher). Each graft was weighed and cut with scissors in the Eppendorf tubes. An equal volume of DMEM medium (W/V) was added to the tubes, and grafts were homogenized with plastic pestles. Tubes with homogenized grafts were vortexed and centrifuged at 12,000 rpm for 10 min RT. Supernatants were transferred into new Eppendorf tubes and used for detection of mouse high sensitivity TNF-α by a Luminex assay. The assay was performed according to the manufacturer's instructions. Levels of peroxidized lipids in grafts were measured in RIPA tissue lysates using a colorimetric TBARS (Thiobarbituric Acid Reactive Substances) Parameter™ kit (R&D Systems) according to the manufacturer's instructions with an exception of preparation of tissue lysates. Preparation of RIPA tissue lysates was done as described in the paragraph below. FIG. 32 shows levels of TNF-α (left graph) and peroxidized lipids (right graph) in adipose grafts excised from nude mice 8 weeks post injection. Data show that implantation of radiated adipose grafts results in an increase of TNF-α and peroxidized lipids, markers of inflammation. There was no inflammation detected in non-radiated grafts (A). The level of inflammation in radiated grafts (B and C) correlates with the radiation dose: moderate inflammation for Graft B and severe inflammation for Graft C, which were radiated by 15 kGy and 30 kGy doses, respectively.

Detection of mouse M2 macrophages and human cells in the human lyophilized devitalized adipose graft's RIPA lysates was performed by Western Blotting (WB) using CD206 and KU-80 antibodies, respectively. Adipose grafts were excised from mice 4 weeks post-injection. Grafts were homogenization samples were incubated for 20 min on wet ice, then centrifugated for 10 min at 4° C. at 12,000 rpm. Cleared lysates were collected in new Eppendorf tubes. Protein concentration was measured in the lysates using the BCA kit (Pierce). Samples for electrophoresis were prepared by mixing lysates with 4× sample buffer and 10×DTT, and then samples were heated for 10 min at 95° C. Prepared samples were loading onto a 4-12% gradient NUPAGE gel at 10 μg protein/lane. Normal mouse white adipose tissue lysate served as a positive control for CD206 (M2 macrophage marker), and THP-1, a human monocyte cell line lysate, served as a positive control for KU-80 (a marker of human cells). After electrophoresis was completed, proteins were transferred onto a PVDF membrane. The membrane was stained with Ponceau S to confirm equal protein load for each lane. Then, the membrane was blocked in the Superblock solution and incubated overnight at 4° C. in the primary antibodies (1:1000 dilution) against mouse M2 macrophages and KU80 antigen. Both antibodies were from Cell Signaling. After overnight incubation, the membrane was washed and incubated with a secondary antibody solution (1:25,000 dilution) for 1 h at RT. The detection of CD206 and KU-80 on the membrane was performed using a femto ECL (Pierce) and an image analyzer. FIG. 14 shows an image of one representative experiment demonstrating that all adipose grafts 4 weeks post injection were populated by mouse M2 macrophages (CD206 marker). There were no human cells detected in adipose grafts (KU-80 marker). Results of WB analysis for M2 macrophages are in agreement with the results of the histological analysis (FIG. 9).

Table 12 summarizes results of in vivo adipose graft testing in nude mice and in vitro testing of grafts excised from nude mice 4 and 8 weeks post-injection. There were no detectable inflammation and encapsulated cysts in non-radiated grafts. Only one non-radiated graft was resorbed (9%). In contrast, radiated tissue grafts have high levels of inflammation and a 45-50% resorption rate. Encapsulated cysts were detected in 2 adipose grafts that received a high radiation dose.

TABLE 12

| Summary of test results for adipose grafts implanted in nude mice | | | |
| --- | --- | --- | --- |
| | Graft Type (Radiation dose in kGy) | | |
| Graft Characteristics | Graft A (0 kGy) | Graft B (15 kGy) | Graft C (30 kGy) | Comments |
| Degraded grafts in % (number of degraded grafts/total number of grafts) | 9% (1/11) | 50% (6/12) | 45% (5/11) | Degradation was defined as >80% reduction in graft weight from the implant on day 0. |
| Encapsulated cysts | 0 | 0 | 2 | Encapsulated cysts are defined as cysts with thick fibrous walls, which likely will be not resorbed |
| Inflammation (TNF-α, pg/mL) | 1.53 +/− 0.60 | 7.47 +/− 3.35 | 291.9 +/− 260.6 | Highest levels of TNF-α in grafts C were detected in grafts with encapsulated cysts |
| Inflammation (Peroxidized lipids, nmol/mg protein) | Below quantitation | 2.6 | 4.9 | Values are for RIPA adipose tissue lysate | transferred in 1.5 mL Eppendorf tubes, cut with scissors, and homogenized with plastic pestles. Then, 0.1 mL/tube RIPA buffer (Cell Signaling) with protease inhibitors (Thermofisher) was added to each tube, and tissues were homogenized again in the RIPA buffer using plastic pestles. After Results of in vitro and in vivo testing of human lyophilized devitalized adipose grafts demonstrate that sterilization by radiation triggers lipid peroxidation in adipose grafts. The level of peroxidized lipids in adipose grafts was dependent of the radiation dose. Implantation of radiated grafts in vivo was associated with a high resorption rate of the grafts and with a formation of encapsulated cysts with a high degree of graft infiltration with inflammatory cells. A high level of inflammation in radiated grafts was confirmed by detection of high levels of inflammatory markers, TNF-α and peroxidized lipids.

In conclusion, obtained results indicate that radiation is not an appropriate method for sterilization of adipose grafts. Results also indicate that levels of peroxidized lipids in adipose grafts might be a predictive marker for clinical outcomes of adipose tissue grafting.

Those skilled in the art will recognize, or be able to ascertain using no more than routine experimentation, many equivalents to the specific embodiments of the method and compositions described herein. Such equivalents are intended to be encompassed by the following claims.

I claim:

1. A composition comprising devitalized adipose tissue and trehalose,
   wherein the devitalized adipose tissue is not decellularized,
   wherein the devitalized adipose tissue comprises at least 50% of native lipids,
   wherein the composition does not comprise free lipids, and
   wherein the devitalized adipose tissue comprises less than 5% native viable cells.

2. The composition of claim 1, wherein the devitalized adipose tissue is minced.

3. The composition of claim 2, wherein the minced devitalized adipose tissue comprises pieces of adipose tissue less than 1 mm in size.

4. The composition of claim 1, wherein the devitalized adipose tissue comprises at least 70% native growth factors.

5. The composition of claim 1, wherein the devitalized adipose tissue retains its native structure.

6. The composition of claim 1, further comprising a pharmaceutically acceptable carrier.

7. The composition of claim 1, wherein the devitalized adipose tissue is cryopreserved or has been previously cryopreserved.

8. The composition of claim 1, wherein the devitalized adipose tissue is lyophilized or has been previously cryopreserved.

9. The composition of claim 1, further comprising human serum albumin.

10. The composition of claim 1, wherein the devitalized adipose tissue comprises less than 5%, 2%, 1%, 0.5%, 0.2%, 0.1%, 0.05% or 0.01% peroxidized lipids of total lipids.

11. A method of augmenting a soft tissue site of a subject in need thereof comprising administering to the subject the composition of claim 1.

12. A method of treating a subject having fat pad atrophy comprising administering to the subject the composition of claim 1.

13. A method of treating a subject having lipodystrophy comprising administering to the subject the composition of claim 1.

14. A method of treating a subject having a metabolic disease or disorder comprising administering to the subject the composition of claim 1.

* * * * *